(12) United States Patent
Yoshizumi et al.

(10) Patent No.: US 8,175,129 B2
(45) Date of Patent: May 8, 2012

(54) GROUP-III NITRIDE SEMICONDUCTOR LASER DEVICE, METHOD OF FABRICATING GROUP-III NITRIDE SEMICONDUCTOR LASER DEVICE, AND METHOD OF ESTIMATING DAMAGE FROM FORMATION OF SCRIBE GROOVE

(75) Inventors: Yusuke Yoshizumi, Itami (JP); Shimpei Takagi, Osaka (JP); Takatoshi Ikegami, Itami (JP); Masaki Ueno, Itami (JP); Koji Katayama, Osaka (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 22 days.

(21) Appl. No.: 12/837,209

(22) Filed: Jul. 15, 2010

(65) Prior Publication Data

US 2011/0164638 A1    Jul. 7, 2011

(30) Foreign Application Priority Data

Jan. 7, 2010   (JP) ................................ P2010-002223

(51) Int. Cl.
*H01S 5/00*   (2006.01)
(52) U.S. Cl. .................................. 372/45.01; 372/44.01
(58) Field of Classification Search ................ 372/44.01, 372/45.01
See application file for complete search history.

(56) References Cited

U.S. PATENT DOCUMENTS

| | | | |
|---|---|---|---|
| 6,653,663 B2 | 11/2003 | Ishida | |
| 7,501,667 B2 | 3/2009 | Hasegawa et al. | |
| 2001/0030328 A1* | 10/2001 | Ishida | 257/103 |
| 2003/0132508 A1 | 7/2003 | Ishida | |
| 2003/0205783 A1 | 11/2003 | Ishida | |
| 2005/0269584 A1 | 12/2005 | Hasegawa et al. | |
| 2008/0230766 A1* | 9/2008 | Okamoto et al. | 257/13 |
| 2009/0059983 A1 | 3/2009 | Hasegawa et al. | |
| 2009/0262771 A1 | 10/2009 | Inoue et al. | |
| 2010/0080001 A1 | 4/2010 | Kunoh et al. | |

FOREIGN PATENT DOCUMENTS

JP   2001-230497 A   8/2001
(Continued)

OTHER PUBLICATIONS

Tyagi et al. "Semipolar (1011) InGaN/GaN Laser Diodes on Bulk GaN Substrates," Japanese Journal of Applied Physics, vol. 46, No. 19 (2007) L444-L445.

*Primary Examiner* — Patrick Stafford
(74) *Attorney, Agent, or Firm* — Venable LLP; Michael A. Sartori

(57) ABSTRACT

A method of fabricating group-III nitride semiconductor laser device includes: preparing a substrate comprising a hexagonal group-III nitride semiconductor and having a semipolar principal surface; forming a substrate product having a laser structure, an anode electrode, and a cathode electrode, where the laser structure includes a semiconductor region and the substrate, where the semiconductor region is formed on the semipolar principal surface; scribing a first surface of the substrate product in a direction of an a-axis of the hexagonal group-III nitride semiconductor to form first and second scribed grooves; and carrying out breakup of the substrate product by press against a second surface of the substrate product, to form another substrate product and a laser bar.

23 Claims, 25 Drawing Sheets

FOREIGN PATENT DOCUMENTS

| | | |
|---|---|---|
| JP | 2005-353690 A | 12/2005 |
| JP | 2007-184353 A | 7/2007 |
| JP | 2008-060555 A | 3/2008 |
| JP | 2008-187044 | 8/2008 |
| JP | 2008-235804 A | 10/2008 |
| JP | 2009-071127 A | 4/2009 |
| JP | 2009-081336 A | 4/2009 |
| JP | 4475357 | 3/2010 |
| JP | 2010-109331 | 5/2010 |

\* cited by examiner

Fig.2
(a)
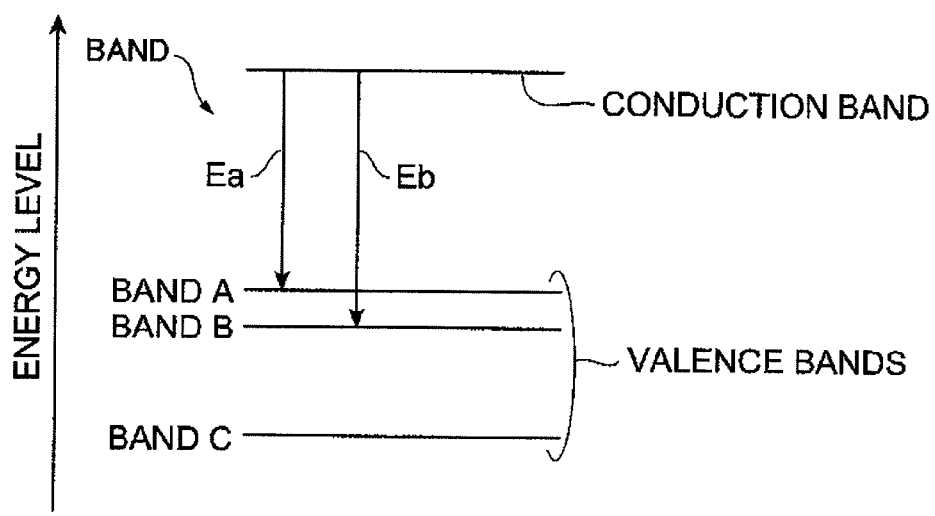
(b)
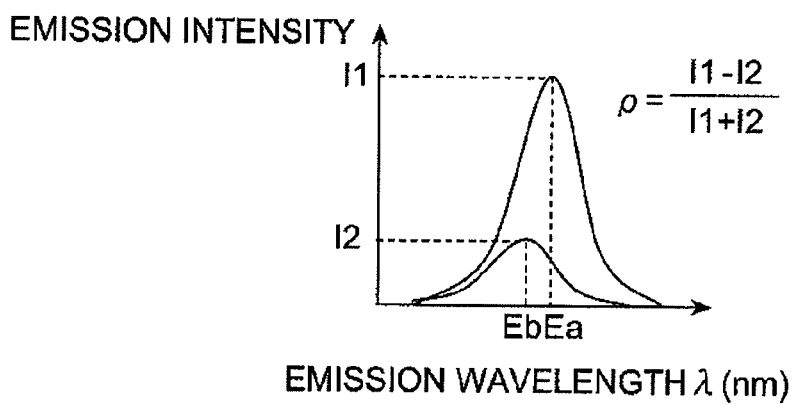

Fig. 6
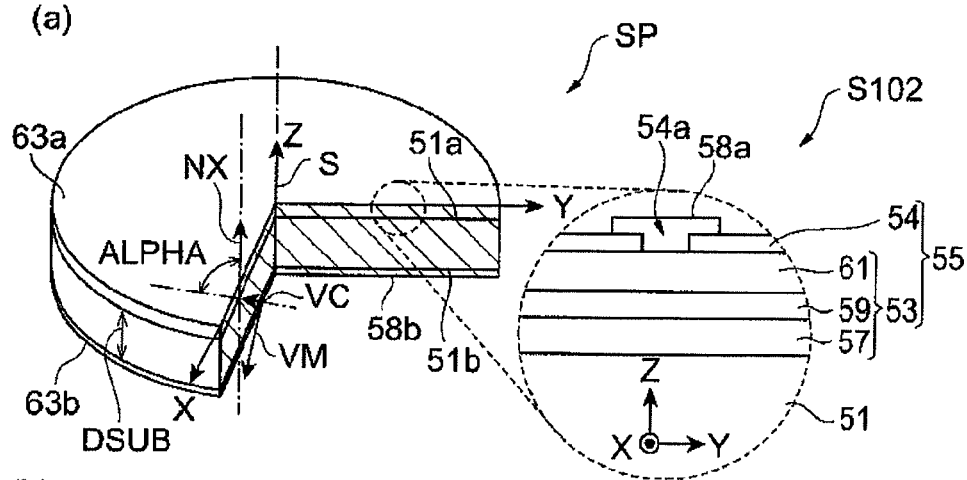
(a)
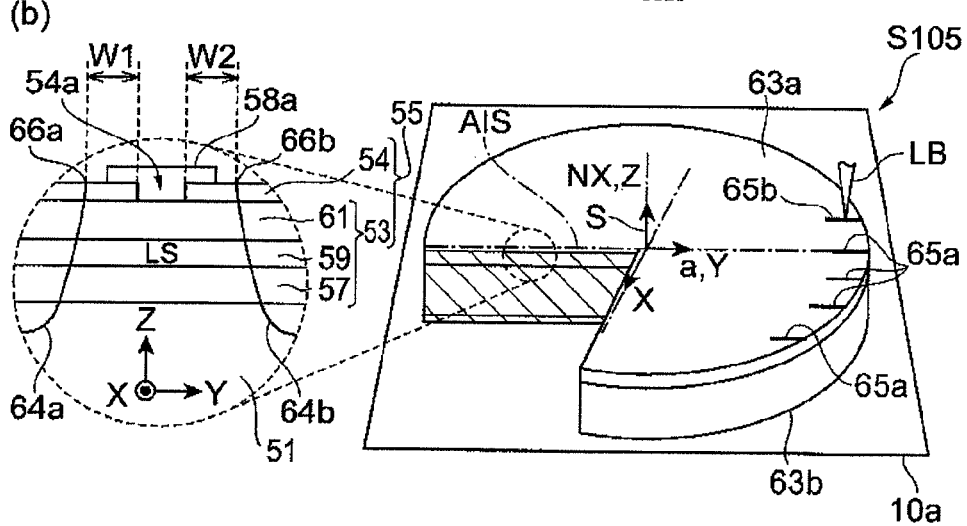
(b)
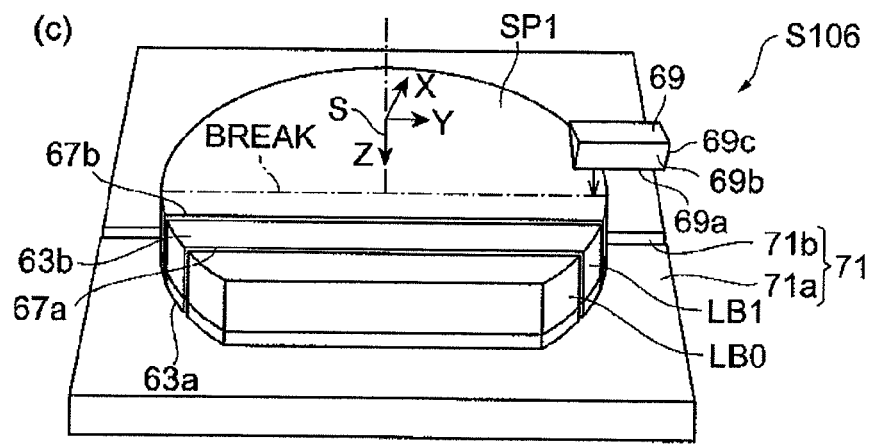
(c)

Fig.7
(a)
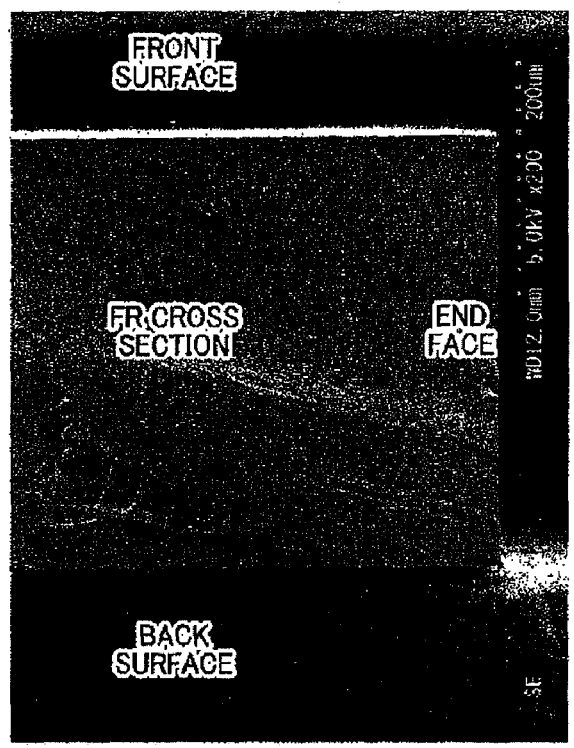
(b)
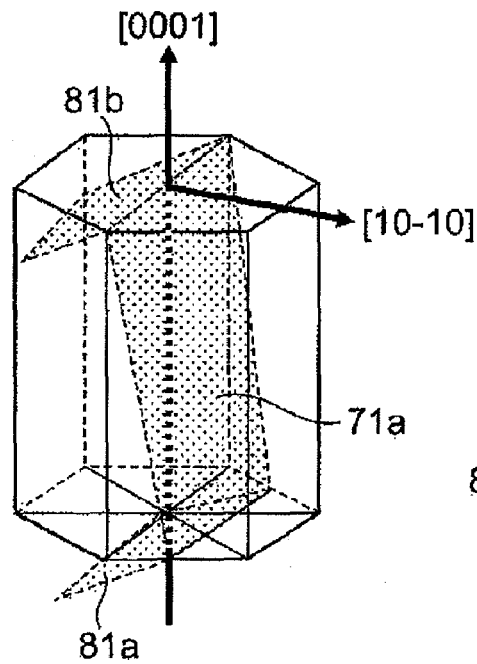
(c)
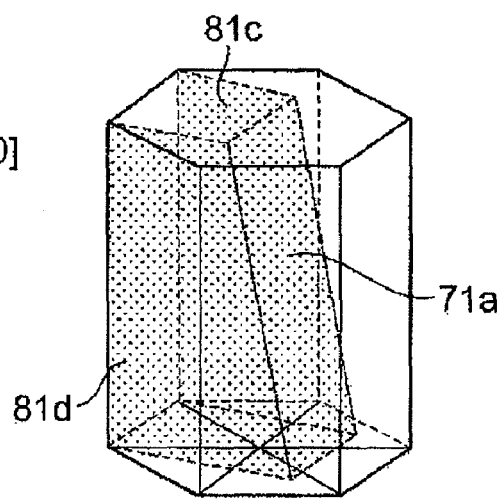

| | Unit: μm | | | | |
|---|---|---|---|---|---|
| chip width | start-side gap | end-side gap | +α margin | groove pitch | groove length |
| 200 | 30 | 10 | 0 | 40 | 160 |
| 200 | 30 | 10 | 10 | 50 | 150 |
| 200 | 30 | 10 | 20 | 60 | 140 |
| 200 | 30 | 10 | 40 | 80 | 120 |
| 200 | 30 | 10 | 60 | 100 | 100 |
| 200 | 30 | 10 | 80 | 120 | 80 |
| 200 | 30 | 10 | 100 | 140 | 60 |
| 200 | 30 | 10 | 120 | 160 | 40 |

(b)

| | Unit: μm | | | | |
|---|---|---|---|---|---|
| chip width | start-side gap | end-side gap | +α margin | groove pitch | groove length |
| 150 | 30 | 10 | 0 | 40 | 110 |
| 150 | 30 | 10 | 10 | 50 | 100 |
| 150 | 30 | 10 | 20 | 60 | 90 |
| 150 | 30 | 10 | 40 | 80 | 70 |
| 150 | 30 | 10 | 70 | 50 | 40 |

(c)

| | Unit: μm | | | | |
|---|---|---|---|---|---|
| chip width | start-side gap | end-side gap | +α margin | groove pitch | groove length |
| 100 | 30 | 10 | 0 | 40 | 60 |
| 100 | 30 | 10 | 10 | 50 | 50 |
| 100 | 30 | 10 | 20 | 60 | 40 |

*Fig.22*

HEXAGONAL GaN

PLANE INDICES OF PLANES PERPENDICULAR TO (20-21)

| a | c | h1 | k1 | l1 | h2 | k2 | l2 | cos θ | Arccos(rad) | (deg) | |
|---|---|---|---|---|---|---|---|---|---|---|---|
| 3.189 | 5.185 | -1 | 0 | 1 | 2 | 0 | 1 | -0.7 | 2.4 | 137.05 | |
| 3.189 | 5.185 | -1 | 0 | 2 | 2 | 0 | 1 | -0.5 | 2.1 | 118.28 | |
| 3.189 | 5.185 | -1 | 0 | 3 | 2 | 0 | 1 | -0.3 | 1.9 | 107.13 | |
| 3.189 | 5.185 | -1 | 0 | 4 | 2 | 0 | 1 | -0.2 | 1.7 | 100.23 | |
| 3.189 | 5.185 | -1 | 0 | 5 | 2 | 0 | 1 | -0.1 | 1.7 | 95.67 | |
| 3.189 | 5.185 | -1 | 0 | 6 | 2 | 0 | 1 | 0.0 | 1.6 | 92.46 | → (-1016) PLANE |
| 3.189 | 5.185 | -1 | 0 | 7 | 2 | 0 | 1 | 0.0 | 1.6 | 90.10 | → (-1017) PLANE |
| 3.189 | 5.185 | -1 | 0 | 8 | 2 | 0 | 1 | 0.0 | 1.5 | 88.29 | → (-1018) PLANE |
| 3.189 | 5.185 | -1 | 0 | 9 | 2 | 0 | 1 | 0.1 | 1.5 | 86.87 | |
| 3.189 | 5.185 | -1 | 0 | 10 | 2 | 0 | 1 | 0.1 | 1.5 | 85.72 | |
| 3.189 | 5.185 | -2 | 0 | 1 | 2 | 0 | 1 | -0.9 | 2.6 | 150.17 | |
| 3.189 | 5.185 | -2 | 0 | 2 | 2 | 0 | 1 | -0.7 | 2.4 | 137.05 | |
| 3.189 | 5.185 | -2 | 0 | 3 | 2 | 0 | 1 | -0.6 | 2.2 | 126.46 | |
| 3.189 | 5.185 | -2 | 0 | 4 | 2 | 0 | 1 | -0.5 | 2.1 | 118.28 | |
| 3.189 | 5.185 | -2 | 0 | 5 | 2 | 0 | 1 | -0.4 | 2.0 | 111.99 | |
| 3.189 | 5.185 | -2 | 0 | 6 | 2 | 0 | 1 | -0.3 | 1.9 | 107.13 | |
| 3.189 | 5.185 | -2 | 0 | 7 | 2 | 0 | 1 | -0.2 | 1.8 | 103.30 | |
| 3.189 | 5.185 | -2 | 0 | 8 | 2 | 0 | 1 | -0.2 | 1.7 | 100.23 | |
| 3.189 | 5.185 | -2 | 0 | 9 | 2 | 0 | 1 | -0.1 | 1.7 | 97.73 | |
| 3.189 | 5.185 | -2 | 0 | 10 | 2 | 0 | 1 | -0.1 | 1.7 | 95.67 | |
| 3.189 | 5.185 | -3 | 0 | 1 | 2 | 0 | 1 | -0.9 | 2.7 | 155.02 | |
| 3.189 | 5.185 | -3 | 0 | 2 | 2 | 0 | 1 | -0.8 | 2.5 | 145.54 | |
| 3.189 | 5.185 | -3 | 0 | 3 | 2 | 0 | 1 | -0.7 | 2.4 | 137.05 | |
| 3.189 | 5.185 | -3 | 0 | 4 | 2 | 0 | 1 | -0.6 | 2.3 | 129.71 | |
| 3.189 | 5.185 | -3 | 0 | 5 | 2 | 0 | 1 | -0.6 | 2.2 | 123.49 | |
| 3.189 | 5.185 | -3 | 0 | 6 | 2 | 0 | 1 | -0.5 | 2.1 | 118.28 | |
| 3.189 | 5.185 | -3 | 0 | 7 | 2 | 0 | 1 | -0.4 | 2.0 | 113.91 | |
| 3.189 | 5.185 | -3 | 0 | 8 | 2 | 0 | 1 | -0.3 | 1.9 | 110.23 | |
| 3.189 | 5.185 | -3 | 0 | 9 | 2 | 0 | 1 | -0.3 | 1.9 | 107.13 | |
| 3.189 | 5.185 | -3 | 0 | 10 | 2 | 0 | 1 | -0.2 | 1.8 | 104.48 | |

GROUP-III NITRIDE SEMICONDUCTOR LASER DEVICE, METHOD OF FABRICATING GROUP-III NITRIDE SEMICONDUCTOR LASER DEVICE, AND METHOD OF ESTIMATING DAMAGE FROM FORMATION OF SCRIBE GROOVE

BACKGROUND OF THE INVENTION

1. Field of the Invention

The present invention relates to a group-III nitride (referred to as III-nitride) semiconductor laser device, a method of fabricating the III-nitride semiconductor laser device, and a method of estimating damage from formation of a scribe groove.

2. Related Background Art

Patent Literature 1 describes a laser device. When a principal surface of a substrate is a face tilting at 28.1° from a {0001} plane toward a direction equivalent to the [1-100] direction, secondary cleaved facets are {11-20} planes perpendicular to both of the principal surface and optical cavity faces, and the laser device is of a rectangular parallelepiped shape.

Patent Literature 2 describes a nitride semiconductor device. The back surface of the substrate for cleavage is polished to reduce the total layer thickness to about 100 μm. A dielectric multilayer film is deposited on cleaved facets.

Patent Literature 3 describes a nitride-based compound semiconductor device. The substrate used for the nitride-based compound semiconductor device comprises a nitride-based compound semiconductor with the threading dislocation density of not more than $3\times10^6$ cm$^{-2}$ and the in-plane threading dislocation density is substantially uniform.

Patent Literature 4 describes a nitride-based semiconductor laser device. In the nitride-based semiconductor laser device, cleaved facets are formed as described below. With respect to recesses which are made by etching from a semiconductor laser device layer to an n-type GaN substrate, scribed grooves are formed like a dashed line (at intervals of about 40 μm) in a direction orthogonal to an extending direction of ridge portions, using a laser scriber, while avoiding projections made during the etching of cavity faces on the n-type GaN substrate. Then the wafer is cleaved at positions of the scribed grooves. On this occasion, each of regions without the scribed grooves, e.g., each projection, is cleaved from the adjacent scribed groove as an origin. As a result, each device separation face is formed as a cleaved facet consisting of a (0001) plane of the n-type GaN substrate.

Patent Literature 5 describes a light emitting device. The light emitting device is able to readily emit light at a long wavelength, without deterioration of luminous efficiency in its light emitting layer.

Patent Literature 6 describes a semiconductor laser. In this semiconductor laser, cleavage introduction level-differences for cleavage having the depth of about 20 μm are formed from the top side of a GaN-based semiconductor laser chip in an n-type GaN substrate, a semiconductor layer, and a current block layer. These cleavage introduction level-differences are spaced by the length of the cavity of the semiconductor laser. These cleavage introduction level-differences are formed only in a region opposite to one side of a ridge part. The distance between the cleavage introduction level-differences and the ridge part (optical waveguide) is not less than about 70 μm. The cleavage introduction level-differences are formed in a direction orthogonal to the ridge part 12a (optical waveguide).

Non-patent Literature 1 describes a semiconductor laser in which a waveguide is provided in an off-axis direction and in which mirrors are made by reactive ion etching, on a semipolar (10-1-1) plane.

Patent Literature 1: Japanese Patent Application Laid-open No. 2001-230497
Patent Literature 2: Japanese Patent Application Laid-open No. 2005-353690
Patent Literature 3: Japanese Patent Application Laid-open No. 2007-184353
Patent Literature 4: Japanese Patent Application Laid-open No. 2009-081336
Patent Literature 5: Japanese Patent Application Laid-open No. 2008-235804
Patent Literature 6: Japanese Patent Application Laid-open No. 2008-060555
Non-patent Literature 1: Jpn. J. Appl. Phys. Vol. 46 (2007) L444

SUMMARY OF THE INVENTION

In the band structure of a GaN-based semiconductor there are some transitions capable of laser oscillation. According to Inventor's knowledge, it is considered that in the III-nitride semiconductor laser device using the semipolar-plane support base the c-axis of which tilts toward the m-axis, the threshold current can be lowered when the laser waveguide extends along a plane defined by the c-axis and the m-axis. When the laser waveguide extends in this orientation, a mode with the smallest transition energy (difference between conduction band energy and valence band energy) among the possible transitions becomes capable of laser oscillation; when this mode becomes capable of laser oscillation, the threshold current can be reduced.

However, this orientation of the laser waveguide does not allow use of the conventional cleaved facets such as c-planes, a-planes, or M-planes for the cavity mirrors. For this reason, the cavity mirrors have been made heretofore by forming dry-etched facets of semiconductor layers by reactive ion etching (RIE). There are now desires for improvement in the cavity mirrors formed by RIE, in terms of perpendicularity to the laser waveguide, flatness of the dry-etched facets, or ion damage. It becomes a heavy burden to derive process conditions for obtaining good dry-etched facets in the current technical level.

As far as the inventor knows, no one has succeeded heretofore in achieving both of the laser waveguide extending in the tilt direction (off-axis direction) of the c-axis and the end faces for cavity mirrors formed without use of dry etching, in the III-nitride semiconductor laser device formed on the semipolar plane.

Patent Literature 6 describes the formation of scribed grooves for cleavage and the minimum distance between the scribed grooves and the ridge part is 70 μM. On the other hand, in the case of a semiconductor laser made on a semipolar plane of a substrate tilting from the c-axis toward the m-axis of a hexagonal III-nitride as in the present application, the end faces for the cavity cannot be produced by making use of cleavage. This semiconductor laser is required to have the laser cavity enabling a low threshold current and is also required to reduce the chip width without significant damage to the laser stripe in forming the laser cavity. The applicant of the present application filed a Japanese patent application (Japanese Patent Application No. 2009-144442) associated with the III-nitride semiconductor laser device including fractured faces for the optical cavity.

The present invention has been accomplished in view of the above-described circumstances. It is an object of the present invention to provide a III-nitride semiconductor laser device with a laser cavity enabling a low threshold current and a structure of ends enabling reduction in chip width at device ends for the laser cavity, on a semipolar plane of a support base tilting from the c-axis toward the m-axis of a hexagonal III-nitride and to provide a method for fabricating the III-nitride semiconductor laser device. It is a further object of the present invention to provide a method for estimating damage from formation of a scribe groove in a semiconductor laser device.

A III-nitride semiconductor laser device according to an aspect of the present invention comprises: (a) a laser structure including a support base comprising a hexagonal III-nitride semiconductor and having a semipolar principal surface, and a semiconductor region provided on the semipolar principal surface of the support base; and (b) an electrode provided on the semiconductor region of the laser structure. The semiconductor region includes a first cladding layer comprising a first conductivity type gallium nitride (GaN)-based semiconductor, a second cladding layer comprising a second conductivity type GaN-based semiconductor, and an active layer provided between the first cladding layer and the second cladding layer; the first cladding layer, the second cladding layer, and the active layer are arranged along a normal axis to the semipolar principal surface; the active layer comprises a GaN-based semiconductor layer; the c-axis of the hexagonal III-nitride semiconductor of the support base tilts at a finite angle ALPHA with respect to the normal axis toward the m-axis of the hexagonal III-nitride semiconductor; the laser structure comprises first and second fractured faces intersecting with an m-n plane defined by the m-axis of the hexagonal III-nitride semiconductor and the normal axis; a laser cavity of the III-nitride semiconductor laser device includes the first and second fractured faces; the laser structure includes first and second surfaces, and the first surface is a surface opposite to the second surface; each of the first and second fractured faces extends from an edge of the first surface to an edge of the second surface.

In the III-nitride semiconductor laser device, the angle between the normal axis and the c-axis of the hexagonal III-nitride semiconductor can be in a range of not less than 45° and not more than 80° or in a range of not less than 100° and not more than 135°.

Furthermore, the semiconductor region is located between the first surface and the substrate, and the laser structure includes a laser stripe extending in a direction of a waveguide axis above the semipolar principal surface of the support base. The waveguide axis extends from one to the other of the first and second fractured faces. The laser structure has first and second recesses provided each at a portion of the edge of the first surface in the first fractured face. The first and second recesses extend from the first surface of the laser structure. Bottom ends of the first and second recesses are located apart from the edge of the second surface of the laser structure. The first recess has an end at the first surface, and the second recess has an end at the first surface. A first distance between the laser stripe and the end of the first recess is smaller than a second distance between the laser stripe and the end of the second recess.

In this III-nitride semiconductor laser device, when the angle is in a range of less than 45° or in a range of more than 135°, end faces made by press are highly likely to be comprised of m-planes. When the angle is in a range of more than 80° and less than 100°, it might result in failing to achieve desired flatness and perpendicularity. Since the first distance between the laser stripe and the end of the first recess can be made smaller than the second distance between the laser stripe and the end of the second recess, the device width of the laser device can be reduced.

In this III-nitride semiconductor laser device, because the first and second fractured faces to form the laser cavity intersect with the m-n plane defined by the m-axis of the hexagonal III-nitride semiconductor and the normal axis, it is feasible to provide the laser waveguide extending in a direction of an intersecting line between the m-n plane and the semipolar plane. Therefore, the present invention succeeds in providing the III-nitride semiconductor laser device with the laser cavity enabling a low threshold current.

In the III-nitride semiconductor laser device according to the present invention, the first and second recesses can be provided along a predetermined plane defined by the a-axis of the hexagonal III-nitride semiconductor and the normal axis. In this III-nitride semiconductor laser device, each of the first and second recesses includes a scribed mark formed from a scribed groove by fracture. The scribed groove guides progress of the fracture, and is divided during the fracture to form the scribed mark in each laser bar. The first and second recesses are provided along the predetermined plane (referred to as "a-n plane").

A III-nitride semiconductor laser device according to an aspect of the present invention comprises: (a) a laser structure including a support base and a semiconductor region, the support base comprising a hexagonal III-nitride semiconductor and having a semipolar principal surface and a back surface, the semiconductor region being provided on the semipolar principal surface of the support base; and (b) an electrode provided on the semiconductor region of the laser structure. The semiconductor region includes a first conductivity type cladding layer, a second conductivity type cladding layer, and an active layer, the active layer being provided between the first cladding layer and the second cladding layer; the first conductivity type cladding layer, the second conductivity type cladding layer, and the active layer are arranged along a normal axis to the semipolar principal surface; the c-axis of the hexagonal III-nitride semiconductor of the support base tilts at an angle ALPHA with respect to the normal axis toward the m-axis of the hexagonal III-nitride semiconductor; the angle ALPHA is in a range of not less than 45° and not more than 80° or in a range of not less than 100° and not more than 135°; the laser structure includes first and second surfaces; the first surface is a surface opposite to the second surface; the semiconductor region is located between the first surface and the support base; the laser structure has first and second scribed marks provided at one end and the other end, respectively, of an edge of the first surface at an end of the laser structure; the first and second scribed marks extend along an a-n plane defined by the a-axis of the hexagonal III-nitride semiconductor and the normal axis; the first and second scribed marks extend from the first surface; the end of the laser structure has a fractured face connecting edges of the first and second scribed marks and edges of the first and second surfaces of the laser structure; a laser cavity of the III-nitride semiconductor laser device includes the fractured face; the laser structure includes a laser stripe extending in a direction of a waveguide axis above the semipolar principal surface of the support base; the first scribed mark has an end at the first surface; the second scribed mark has an end at the first surface; a first distance between the laser stripe and the end of the first scribed mark is smaller than a second distance between the laser stripe and the end of the second scribed mark.

In this III-nitride semiconductor laser device, when the angle is in a range of less than 45° or in a range of more than 135°, an end face formed by press is highly likely to be comprised of an m-plane. When the angle is in a range of more than 80° and less than 100°, the desired flatness and perpendicularity might not be achieved. Each of the first and second scribed marks is formed from a scribed groove by fracture, and the scribed groove guides progress of the fracture. Furthermore, since the first distance between the laser stripe and the end of the first scribed mark can be made smaller than the second distance between the laser stripe and the end of the second scribed mark, the device width of the laser device can be reduced.

In the III-nitride semiconductor laser device according to the present invention, the first distance can be not less than 20 μm. In this III-nitride semiconductor laser device, the end of the recess can be located up to the close distance of 20 μm from the laser stripe. The first distance can be less than 50 μm. In this III-nitride semiconductor laser device, when the first distance is less than 50 μm, it promises contribution to reduction in device width.

In the III-nitride semiconductor laser device according to the present invention, the first distance can be less than 50 μm and the second distance can be not less than 50 μm. In this III-nitride semiconductor laser device, the device width of the laser device can be reduced because the first distance can be made smaller than the second distance.

In the III-nitride semiconductor laser device according to the present invention, a width of the III-nitride semiconductor laser device can be not more than 200 μm. This III-nitride semiconductor laser device can provide the device width of not more than 200 μm.

In the III-nitride semiconductor laser device according to the present invention, more preferably, the angle between the normal axis and the c-axis of the hexagonal III-nitride semiconductor falls within a range of not less than 63° and not more than 80° or within a range of not less than 100° and not more than 117°.

In this III-nitride semiconductor laser device, when the angle is in a range of not less than 63° and not more than 80° or in a range of not less than 100° and not more than 117°, end faces made by press are highly likely to be faces nearly perpendicular to the principal surface of the substrate. When the angle is in a range of more than 80° and less than 100°, it might result in failing to achieve the desired flatness and perpendicularity.

In the III-nitride semiconductor laser device according to the present invention, a thickness of the support base is preferably not more than 400 μm. This III-nitride semiconductor laser device is suitable for obtaining good-quality fractured faces for the laser cavity.

In the III-nitride semiconductor laser device according to the present invention, more preferably, a thickness of the support base is not less than 50 μm and not more than 100 μm. When the thickness is not less than 50 μm, handling becomes easier, and production yield becomes higher. When the thickness is not more than 100 μm, it is more suitable for obtaining good-quality fractured faces for the laser cavity.

In the III-nitride semiconductor laser device according to the present invention, laser light from the active layer is polarized in a direction of the a-axis of the hexagonal III-nitride semiconductor. In this III-nitride semiconductor laser device, a band transition allowing for achievement of a low threshold current has polarized nature.

In the III-nitride semiconductor laser device according to the present invention, light in the LED mode in the III-nitride semiconductor laser device includes a polarization component I1 in the direction of the a-axis of the hexagonal III-nitride semiconductor, and a polarization component I2 in a projected direction of the c-axis of the hexagonal III-nitride semiconductor on the principal surface, and the polarization component I1 is greater than the polarization component I2. This III-nitride semiconductor laser device can lase with the laser cavity to emit light in a mode with large emission intensity in the LED mode.

In the III-nitride semiconductor laser device according to the present invention, preferably, the semipolar principal surface is one of a {20-21} plane, a {10-11} plane, a {20-2-1} plane, and a {10-1-1} plane.

This III-nitride semiconductor laser device allows for provision of first and second end faces with flatness and perpendicularity enough to construct the laser cavity of the III-nitride semiconductor laser device, on these typical semipolar planes.

In the III-nitride semiconductor laser device according to the present invention, the semipolar principal surface suitably applicable is a surface with a slight slant in a range of not less than −4° and not more than +4° from any one semipolar plane of a {20-21} plane, a {10-11} plane, a {20-2-1} plane, and a {10-1-1} plane, toward an m-plane.

This III-nitride semiconductor laser device allows for provision of the first and second end faces with flatness and perpendicularity enough to construct the laser cavity of the III-nitride semiconductor laser device, on the slight slant surface from these typical semipolar planes.

In the III-nitride semiconductor laser device according to the present invention, preferably, a stacking fault density of the support base is not more than $1 \times 10^4$ cm$^{-1}$.

In this III-nitride semiconductor laser device, because the stacking fault density is not more than $1 \times 10^4$ cm$^{-1}$, the flatness and/or perpendicularity of the fractured faces is unlikely to be disturbed for a certain accidental reason.

In the III-nitride semiconductor laser device according to the present invention, the support base can comprise any one of GaN, AlGaN, AlN, InGaN, and InAlGaN.

In this III-nitride semiconductor laser device, when the substrate used comprises one of these GaN-based semiconductors, it becomes feasible to obtain the first and second end faces applicable to the cavity. Use of an AlN substrate or AlGaN substrate allows for increase in degree of polarization and enhancement of optical confinement by virtue of low refractive index. Use of an InGaN substrate allows for decrease in lattice mismatch rate between the substrate and the light emitting layer and improvement in crystal quality.

The III-nitride semiconductor laser device according to the present invention can further comprise a dielectric multilayer film provided on at least one of the first and second fractured faces.

In this III-nitride semiconductor laser device, an end face coat is also applicable to the fractured faces. The end face coat allows for adjustment of reflectance.

In the III-nitride semiconductor laser device according to the present invention, the active layer can include a quantum well structure provided so as to generate light at a wavelength of not less than 430 nm and not more than 600 nm. Since this III-nitride semiconductor laser device makes use of the semipolar plane, the resultant device is the III-nitride semiconductor laser device making efficient use of polarization in the LED mode, and achieves a low threshold current.

In the III-nitride semiconductor laser device according to the present invention, more preferably, the active layer includes a quantum well structure provided so as to generate light at a wavelength of not less than 500 nm and not more than 600 nm. Since this III-nitride semiconductor laser device makes use of the semipolar plane, it allows for increase in quantum efficiency through decrease of the piezoelectric field and improvement in crystal quality of the light emitting layer region and it is thus suitably applicable to generation of light at the wavelength of not less than 500 nm and not more than 600 nm.

In the III-nitride semiconductor laser device according to the present invention, an end face of the support base and an end face of the semiconductor region are exposed in each of the first and second fractured faces, and an angle between the end face of the semiconductor region in the active layer and a reference plane perpendicular to the m-axis of the support base comprising the hexagonal nitride semiconductor is an angle in a range of not less than (ALPHA−5)° and not more than (ALPHA+5)° on a first plane defined by the c-axis and the m-axis of the III-nitride semiconductor.

This III-nitride semiconductor laser device has the end faces satisfying the foregoing perpendicularity, concerning the angle taken from one to the other of the c-axis and the m-axis.

In the III-nitride semiconductor laser device according to the present invention, preferably, the angle is in a range of not less than −5° and not more than +5° on a second plane perpendicular to the first plane and the normal axis.

This III-nitride semiconductor laser device has the end faces satisfying the foregoing perpendicularity, concerning the angle defined on the plane perpendicular to the normal axis to the semipolar plane.

In the III-nitride semiconductor laser device according to the present invention, the electrode extends in a direction of a predetermined axis, and the first and second fractured faces intersect with the predetermined axis.

In the III-nitride semiconductor laser device according to the present invention, the laser structure can further comprise an insulating film with an aperture, the insulating film being provided on the semiconductor region. The electrode is connected through the aperture of the insulating film to the semiconductor region of the laser structure. The first distance can be defined by a distance between the aperture of the insulating film and the end of the first recess, and the second distance can be defined by a distance between the aperture of the insulating film and the end of the second recess. In this III-nitride semiconductor laser device, each of the first and second distances is defined by the distance between the aperture of the insulating film and the end of the first and second recesses. In the III-nitride semiconductor laser device according to the present invention, the aperture of the insulating film can have, for example, a stripe shape.

In the III-nitride semiconductor laser device according to the present invention, the semiconductor region of the laser structure can have a ridge structure. The first distance can be defined by a distance between the ridge structure and the end of the first recess, and the second distance can be defined by a distance between the ridge structure and the end of the second recess. In this III-nitride semiconductor laser device, each of the first and second distances is defined by the distance between the ridge structure and the end of the first and second recesses.

In the III-nitride semiconductor laser device according to the present invention, preferably, the first recess includes a slope portion where the bottom end of the first recess tilts toward the end of the first recess; the second recess includes a slope portion where the bottom end of the second recess tilts toward the end of the second recess; a first length of the slope portion of the first recess is longer than a second length of the slope portion of the second recess. In this III-nitride semiconductor laser device, the scribed groove is formed so that the first length is longer than the second length, whereby it becomes feasible to reduce an adverse effect on laser operation from damage near the end of the first recess with damage greater than damage at the end of the second recess.

Another aspect of the present invention relates to a method for fabricating a III-nitride semiconductor laser device. This method comprises: (a) a step of preparing a substrate comprising a hexagonal III-nitride semiconductor and having a semipolar principal surface; (b) a step of forming a substrate product having a laser structure, an anode electrode, and a cathode electrode, the laser structure including a semiconductor region and the substrate, the semiconductor region being formed on the semipolar principal surface; (c) a step of scribing a first surface of the substrate product in a direction of the a-axis of the hexagonal III-nitride semiconductor to form first and second scribed grooves; and (d) a step of carrying out breakup of the substrate product by press against a second surface of the substrate product, to form another substrate product and a laser bar. The first surface is a surface opposite to the second surface; the semiconductor region is located between the first surface and the substrate; the laser bar has first and second end faces extending from the first surface to the second surface and made by the breakup; the first and second end faces form a laser cavity of the III-nitride semiconductor laser device; the anode electrode and the cathode electrode are formed on the laser structure; the semiconductor region includes a first cladding layer comprising a first conductivity type GaN-based semiconductor, a second cladding layer comprising a second conductivity type GaN-based semiconductor, and an active layer provided between the first cladding layer and the second cladding layer; the first cladding layer, the second cladding layer, and the active layer are arranged along a normal axis to the semipolar principal surface; the active layer includes a GaN-based semiconductor layer; the c-axis of the hexagonal III-nitride semiconductor of the substrate tilts at a finite angle ALPHA with respect to the normal axis toward the m-axis of the hexagonal III-nitride semiconductor; the first and second end faces intersect with an m-n plane defined by the m-axis of the hexagonal III-nitride semiconductor and the normal axis. The angle ALPHA is in a range of not less than 45° and not more than 80° or in a range of not less than 100° and not more than 135°.

In this method, the substrate product includes a laser stripe extending above the semipolar principal surface; the laser stripe extends in a direction of a waveguide axis; the waveguide axis extends from one to the other of the first and second end faces; and the first scribed groove, the laser stripe, and the second scribed groove are arranged in order in a direction of the a-axis of the hexagonal III-nitride semiconductor. The first scribed groove has an end at the first surface and the second scribed groove has an end at the first surface. A first distance between the laser stripe and the end of the first scribed groove is smaller than a second distance between the laser stripe and the end of the second scribed groove and a distance between the end of the first scribed groove and the end of the second scribed groove is smaller than a width of the III-nitride semiconductor laser device.

According to this method, the first surface of the substrate product is scribed in the direction of the a-axis of the hexagonal III-nitride semiconductor and thereafter the breakup of the substrate product is carried out by press against the second surface of the substrate product, thereby forming the other substrate product and the laser bar. For this reason, the first and second end faces are formed in the laser bar so as to intersect the m-n plane defined by the m-axis of the hexagonal III-nitride semiconductor and the normal axis. This end face forming method provides as the first and second end faces, cavity mirror faces with flatness and perpendicularity enough to construct the laser cavity of the III-nitride semiconductor laser device, or without ion damage.

In this method, the laser waveguide extends in a direction of tilt of the c-axis of the hexagonal III-nitride, and the mirror end faces of the cavity capable of providing this laser waveguide are formed without use of dry-etched facets. In this method, when the angle is in a range of less than 45° or in a range of more than 135°, the end faces made by press are highly likely to be comprised of m-planes. When the angle is in a range of more than 80° and less than 100°, it might result in failing to achieve the desired flatness and perpendicularity.

In this method, the scribed grooves and laser stripes can be alternately arranged in the a-axis direction on the substrate product. A scribed groove is formed between two adjacent laser stripes. Damage due to formation of a scribed groove is not isotropic near the scribed groove. Namely, a damaged region due to formation of a scribed groove is formed in asymmetry near the scribed groove. For this reason, the size of the damaged region near one end of the scribed groove is smaller than that of the damaged region near the other end of the scribed groove. When attention is focused on one laser stripe among the array of laser stripes, the first distance (distance between the laser stripe and the end of the first scribed groove) can be made smaller than the second distance (distance between the laser stripe and the end of the second scribed groove). For this reason, the device width of the laser device can be reduced.

In the method according to the present invention, the first distance can be not less than 20 µm. According to this method, the size of the damaged region near one end of the scribed groove is smaller than the size of the damaged region near the other end of the scribed groove on the substrate product. The end of the scribed groove with the smaller size of the damaged region can be located up to the minimum distance of about 20 µm from the laser stripe. In the method according to the present invention, the first distance can be less than 50 µm. In this method, the end of the scribed groove with the smaller size of the damaged region can be located up to the close distance of about 50 µm from the laser stripe.

In the method according to the present invention, the first distance can be less than 50 µm and the second distance can be not less than 50 µm. In this method, the adjacent scribed grooves are formed so that the first distance is smaller than the second distance, which can reduce the device width of the laser device.

In the method according to the present invention, a width of the III-nitride semiconductor laser device can be not more than 200 µm. In this method, the laser device can be formed in the device width of not more than 200 µm.

In the method according to the present invention, the step of forming the substrate product comprises performing processing such as slicing or grinding of the substrate so that a thickness of the substrate becomes not more than 400 µm, and the second surface can be a processed surface made by the processing. Alternatively, it can be a surface including an electrode formed on the processed surface.

In the method according to the present invention, the step of forming the substrate product comprises polishing the substrate so that the thickness of the substrate becomes not less than 50 µm and not more than 100 µm, and the second surface can be a polished surface formed by the polishing. Alternatively, it can be a surface including an electrode formed on the polished surface.

With the substrate in such thickness, it is feasible to form the first and second end faces with flatness and perpendicularity enough to construct the laser cavity of the III-nitride semiconductor laser device, or without ion damage, in good yield.

In the method according to the present invention, more preferably, the angle ALPHA can fall within a range of not less than 63° and not more than 80° or within a range of not less than 100° and not more than 117°. When the angle is in a range of less than 63° or in a range of more than 117°, an m-plane can appear in part of an end face made by press. When the angle is in a range of more than 80° and less than 100°, the desired flatness and perpendicularity are not achieved.

In the method according to the present invention, preferably, the semipolar principal surface is any one of a {20-21} plane, a {10-11} plane, a {20-2-1} plane, and a {10-1-1} plane.

With these semipolar planes, it is also feasible to provide the first and second end faces with flatness and perpendicularity enough to construct the laser cavity of the III-nitride semiconductor laser device, or without ion damage.

In the method according to the present invention, the semipolar principal surface suitably applicable is a surface with a slight slant in a range of not less than −4° and not more than +4° from any one semipolar plane of a {20-21} plane, a {10-11} plane, a {20-2-1} plane, and a {10-1-1} plane, toward the m-plane.

With the slight slant surface from these typical semipolar planes, it is also feasible to provide the first and second end faces with flatness and perpendicularity enough to construct the laser cavity of the III-nitride semiconductor laser device, or without ion damage.

In the method according to the present invention, the scribing is carried out using a laser scriber, the scribing forms a scribed groove, and a length of the scribed groove is shorter than a length of an intersecting line between an a-n plane defined by the a-axis of the hexagonal III-nitride semiconductor and the normal axis, and the first surface.

According to this method, the other substrate product and the laser bar are formed by fracture of the substrate product. This fracture is brought about by using the scribed groove shorter than a fracture line of the laser bar.

In the method according to the present invention, an end face of the active layer in each of the first and second end faces can make an angle in a range of not less than (ALPHA−5)° and not more than (ALPHA+5)° on a plane defined by the c-axis and the m-axis of the hexagonal III-nitride semiconductor, with respect to a reference plane perpendicular to the m-axis of the support base comprising the hexagonal nitride semiconductor.

This method allows for forming the end faces with perpendicularity as mentioned above, as to the angle taken from one to the other of the c-axis and the m-axis.

In the method according to the present invention, the substrate can comprise any one of GaN, AlN, AlGaN, InGaN, and InAlGaN. This method allows the first and second end faces applicable to the cavity to be obtained through the use of the substrate comprising one of these GaN-based semiconductors.

In the method according to the present invention, the laser structure can further include an insulating film having an aperture and provided on the semiconductor region. The electrode is connected through the aperture of the insulating film to the semiconductor region of the laser structure; the first distance can be defined by a distance between the aperture of the insulating film and the end of the first scribed groove. In this method, each of the first and second distances is defined by the distance between the aperture of the insulating film and the end of the first and second recesses. The electrode is in contact with the semiconductor region through the aperture of the insulating film. This contact defines an area where carriers flow from the electrode into the semiconductor region. The carriers contribute to emission through recombination in the active layer.

In the method according to the present invention, the semiconductor region of the laser structure can have a ridge structure; the first distance can be defined by a distance between the ridge structure and the end of the first scribed groove. In this method, each of the first and second distances is defined by the distance between the ridge structure and the end of the first and second recesses. Carriers flowing from the electrode into the semiconductor region are guided to the ridge structure. This ridge structure defines a range where carriers flow from the electrode into the semiconductor region. The carriers contribute to emission through recombination in the active layer.

Still another aspect of the present invention is a method of estimating damage from formation of a scribe groove. This method comprises: (a) a step of forming a groove in a semiconductor device including a hexagonal III-nitride semiconductor, using a device for forming a scribed groove; (b) a step of obtaining an image of a region including the groove of the semiconductor device, using either of a scanning electron microscope and a cathodoluminescence measuring device for the semiconductor device, after formation of the groove; and (c) a step of making an estimation on a level of damage near the groove, based on the image. The semiconductor device includes a substrate comprising a hexagonal III-nitride semiconductor and a hexagonal III-nitride semiconductor region formed on the substrate, or includes a substrate comprising a hexagonal III-nitride semiconductor.

According to this method, there appears a difference according to the damage due to the formation of the scribed groove in the image of the region near the groove, which is obtained with either of the scanning electron microscope and the cathodoluminescence measuring device. The estimation on the level of damage near the groove can be made based on the image obtained with the scanning electron microscope or the cathodoluminescence measuring device.

The method according to the foregoing aspect of the present invention can further comprise a step of determining a distance between an end of the scribed groove and a laser stripe of a semiconductor laser, based on the estimation. In this method, the distance between the scribed groove and the laser stripe can be determined based on the estimating damage from formation of the scribe groove.

A further aspect of the present invention relates to a method for fabricating a III-nitride semiconductor laser device. This method comprises: (a) a step of forming a groove in a semiconductor device including a hexagonal III-nitride semiconductor, using a device for formation of a scribed groove; (b) a step of obtaining an image of a region including the groove of the semiconductor device, using either of a scanning electron microscope and a cathodoluminescence measuring device for the semiconductor device, after formation of the groove; (c) a step of making an estimation on a level of damage near the groove, based on the image; (d) a step of forming a substrate product for a III-nitride semiconductor laser device, based on the estimation; (e) a step of forming a scribed groove in the substrate product, using a condition of the forming; and (f) a step of performing breakup of the substrate product by press against the substrate product, after formation of the scribed groove in the substrate product. The semiconductor device includes a substrate comprising a hexagonal III-nitride semiconductor and a hexagonal III-nitride semiconductor region formed on the substrate, or includes a substrate comprising a hexagonal III-nitride semiconductor.

According to this method, the scribed groove can be formed in the substrate product, based on the estimation. For this reason, a minimum distance between an end of the scribed groove formed under the foregoing forming condition and a laser stripe of a semiconductor laser can be determined based on the estimation.

In the further aspect of the present invention, the substrate product has a laser structure, an anode electrode, and a cathode electrode, the laser structure including a substrate and a semiconductor region, the substrate comprising a hexagonal III-nitride semiconductor, the semiconductor region being formed on a semipolar principal surface of the substrate. The c-axis of the hexagonal III-nitride semiconductor of the substrate tilts at an angle ALPHA with respect to the normal axis toward the m-axis of the hexagonal III-nitride semiconductor, and the angle ALPHA can be in a range of not less than 45° and not more than 80° or in a range of not less than 100° and not more than 135°.

A III-nitride semiconductor laser device according to an aspect of the present invention comprises: (a) a laser structure including a support base comprising a hexagonal III-nitride semiconductor and having a semipolar principal surface and a back surface, and a semiconductor region provided on the semipolar principal surface of the support base; and (b) an electrode provided on the semiconductor region of the laser structure. The semiconductor region includes a first conductivity type cladding layer, a second conductivity type cladding layer, and an active layer provided between the first cladding layer and the second cladding layer; the first conductivity type cladding layer, the second conductivity type cladding layer, and the active layer are arranged along a normal axis to the semipolar principal surface; the c-axis of the hexagonal III-nitride semiconductor of the support base tilts at an angle ALPHA with respect to the normal axis toward the axis of the hexagonal III-nitride semiconductor; the angle ALPHA is in a range of not less than 45° and not more than 80° or in a range of not less than 100° and not more than 135°; the laser structure includes first and second surfaces; the first surface is a surface opposite to the second surface; the semiconductor region is located between the first surface and the support base; the laser structure has first and second scribed marks at one end and the other end, respectively, of an edge of the first surface at an end of the laser structure; the first and second scribed marks extend from the first surface; the end of the laser structure has a fractured face connecting edges of the first and second scribed marks and the edges of the first and second surfaces of the laser structure; a laser cavity of the III-nitride semiconductor laser device includes the fractured face; the first and second scribed marks extend along a predetermined plane defined by the a-axis of the hexagonal III-nitride semiconductor and the normal axis.

In this III-nitride semiconductor laser device, the first and second scribed marks are provided along the predetermined plane (referred to as "a-n plane"). These scribed marks are formed from scribed grooves. The scribed grooves guide progress of fracture. For this reason, the fracture proceeds in the direction of the a-n plane to form the fractured face. In this III-nitride semiconductor laser device, the fractured face for the laser cavity intersects with an m-n plane defined by the m-axis of the hexagonal III-nitride semiconductor and the normal axis, and therefore a laser waveguide can be provided so as to extend in a direction of an interesting line between the m-n plane and the semipolar plane. For this reason, it is feasible to provide the III-nitride semiconductor laser device with the laser cavity enabling a low threshold current.

Furthermore, in this III-nitride semiconductor laser device, when the angle is in a range of less than 45° or in a range of more than 135°, an end face formed by press is highly likely to be comprised of an m-plane. When the angle is in a range of more than 80° and less than 100°, the desired flatness and perpendicularity might not be achieved. Therefore, this III-nitride semiconductor laser device can be provided as the III-nitride semiconductor laser device with the laser cavity enabling the low threshold current, on the semipolar plane of the support base tilting from the c-axis toward the m-axis of the hexagonal III-nitride.

The above objects and the other objects, features, and advantages of the present invention can more readily become apparent in view of the following detailed description of the preferred embodiments of the present invention proceeding with reference to the accompanying drawings.

BRIEF DESCRIPTION OF THE DRAWINGS

FIG. 2 is a drawing showing a band structure in an active layer in the III-nitride semiconductor laser device.

FIG. 6 is a drawing schematically showing major steps in the method for fabricating the III-nitride semiconductor laser device according to the embodiment.

FIG. 7 is a drawing showing a scanning electron microscope image of a cavity end face, along with a {20-21} plane in crystal lattices.

FIG. 17 is a drawing showing a list of dimensions used in an experiment in formation of scribed grooves for obtaining chip widths of 200 μm, 150 μm, and 100 μm.

FIG. 22 is a drawing showing angles between (20-21) plane and other plane orientations (indices).

DETAILED DESCRIPTION OF THE PREFERRED EMBODIMENTS

The expertise of the present invention can be readily understood in view of the following detailed description with reference to the accompanying drawings provided by way of illustration only. The following will describe embodiments of the III-nitride semiconductor laser device and the method for fabricating the III-nitride semiconductor laser device according to the present invention, with reference to the accompanying drawings. The same portions will be denoted by the same reference symbols as much as possible.

Figure 1:
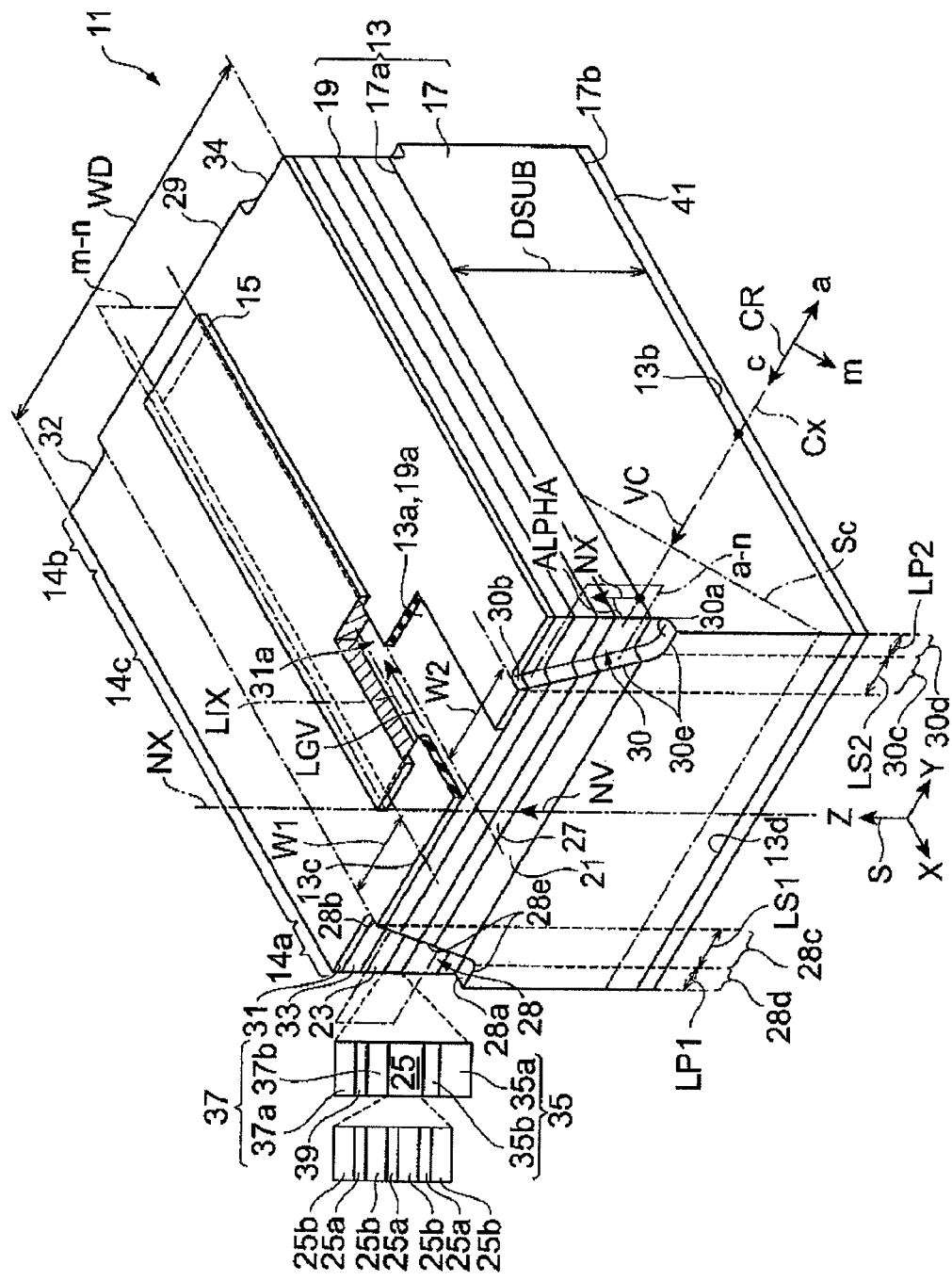
FIG. 1 is a drawing schematically showing a structure of a III-nitride semiconductor laser device according to an embodiment of the present invention.

FIG. 1 is a drawing schematically showing a structure of a III-nitride semiconductor laser device according to an embodiment of the present invention. The III-nitride semiconductor laser device 11 has a gain-guiding type structure, but embodiments of the present invention are not limited to the gain-guiding type structure. The III-nitride semiconductor laser device 11 has a laser structure 13 and an electrode 15. The laser structure 13 includes a support base 17 and a semiconductor region 19. The support base 17 comprises a hexagonal III-nitride semiconductor and has a semipolar principal surface 17a and a back surface 17b. The semiconductor region 19 is provided on the semipolar principal surface 17a of the support base 17. The electrode 15 is provided on the semiconductor region 19 of the laser structure 13. The semiconductor region 19 includes a first cladding layer 21, a second cladding layer 23, and an active layer 25. The first cladding layer 21 comprises a first conductivity type GaN-based semiconductor, e.g., n-type AlGaN, n-type InAlGaN, or the like. The second cladding layer 23 comprises a second conductivity type GaN-based semiconductor, e.g., p-type AlGaN, p-type InAlGaN, or the like. The active layer 25 is provided between the first cladding layer 21 and the second cladding layer 23. The active layer 25 includes GaN-based semiconductor layers, and the GaN-based semiconductor layers are, for example, well layers 25a. The active layer 25 includes barrier layers 25b comprising a GaN-based semiconductor, and the well layers 25a and the barrier layers 25b are alternately arranged. The well layers 25a comprise, for example, InGaN or the like, and the barrier layers 25b, for example, GaN, InGaN, or the like. The active layer 25 can include a quantum well structure provided so as to generate light at the wavelength of not less than 430 nm and not more than 600 nm. Use of a semipolar plane is suitable for generation of light at the wavelength of not less than 500 nm (green) and not more than 600 nm. The transverse spread of light in the optical waveguide is related to the wavelength of guided light. The distances W1, W2 according to the present embodiment are suitably applicable in the aforementioned wavelength range. The first cladding layer 21, the second cladding layer 23, and the active layer 25 are arranged along a normal axis NX to the semipolar principal surface 17a. In the III-nitride semiconductor laser device 11, the laser structure 13 includes a first fractured face 27 and a second fractured face 29 intersecting with an m-n plane defined by the m-axis of the hexagonal III-nitride semiconductor and the normal axis NX.

Referring to FIG. 1, there are an orthogonal coordinate system S and a crystal coordinate system CR depicted. The normal axis NX is directed along a direction of the Z-axis of the orthogonal coordinate system S. The semipolar principal surface 17a extends in parallel with a predetermined plane defined by the X-axis and the Y-axis of the orthogonal coordinate system S. In FIG. 1, a typical c-plane Sc is also depicted. The c-axis of the hexagonal III-nitride semiconductor of the support base 17 tilts at a finite angle ALPHA with respect to the normal axis NX toward the m-axis of the hexagonal III-nitride semiconductor.

The III-nitride semiconductor laser device 11 further has an insulating film 31. The insulating film 31 covers a surface 19a of the semiconductor region 19 of the laser structure 13, and the semiconductor region 19 is located between the insulating film 31 and the support base 17. The support base 17 comprises a hexagonal III-nitride semiconductor. The insulating film 31 has an aperture 31a, and the aperture 31a extends in a direction of an intersecting line LIX between the surface 19a of the semiconductor region 19 and the foregoing m-n plane and is, for example, a stripe shape. The electrode 15 is in contact with the surface 19a of the semiconductor region 19 (e.g., a contact layer 33 of the second conductivity type) through the aperture 31a and extends in the direction of the foregoing intersecting line LIX. In the III-nitride semiconductor laser device 11, a laser waveguide includes the first cladding layer 21, the second cladding layer 23, and the active layer 25, and extends in the direction of the foregoing intersecting line LIX. For example, in the case of a gain guiding type laser, the aperture 31a of the insulating film 31 has, for example, the stripe shape, and the direction of the laser waveguide is the extending direction of the stripe aperture. In the case of a ridge type laser, the semiconductor region 19 of the laser structure 13 has the ridge structure, and the direction of the laser waveguide is the extending direction of the ridge structure. A waveguide vector LGV shows the direction of the laser waveguide.

In the III-nitride semiconductor laser device 11, the first fractured face 27 and the second fractured face 29 intersect with the m-n plane defined by the m-axis of the hexagonal III-nitride semiconductor and the normal axis NX. A laser cavity of the III-nitride semiconductor laser device 11 includes the first and second fractured faces 27, 29, and the laser waveguide extends from one to the other of the first fractured face 27 and the second fractured face 29. The laser structure 13 includes a first surface 13a and a second surface 13b, and the first surface 13a is a surface opposite to the second surface 13b. The first and second fractured faces 27, 29 each extend from an edge 13c of the first surface 13a to an edge 13d of the second surface 13b. The first and second fractured faces 27, 29 are different from the conventional cleaved facets such as c-planes, m-planes, or a-planes. The semiconductor region 17 is located between the first surface 13a and the support base 17 (or substrate). The laser structure 13 includes a laser stripe extending in a direction of a waveguide axis above the semipolar principal surface 17a of the support base 17. The waveguide axis extends from one to the other of the first and second fractured faces 27, 29. The waveguide axis is directed in the direction of the waveguide vector LGV extending in the direction from the first fractured face 27 to the second fractured face 29.

In this III-nitride semiconductor laser device 11, the first and second fractured faces 27, 29 forming the laser cavity intersect with the m-n plane. This allows for provision of the laser waveguide extending in the direction of the intersecting line between the m-n plane and the semipolar plane 17a. For this reason, the III-nitride semiconductor laser device 11 has the laser cavity enabling a low threshold current.

The laser structure 13 has first and second recesses 28, 30 provided each at a portion of edge 13c of the first surface 13a in a fractured face (reference is made to the "first fractured face 27" in the description hereinafter). The first and second recesses 28, 30 include first and second scribed marks, respectively, left in each semiconductor device separated by fracture guided by scribed grooves. The first and second recesses 28, 30 extend from the first surface 13a of the laser structure 13. Bottom ends 28a, 30a of the first and second recesses 28, are located apart from edge 13d of the second surface 13b of the laser structure. The first recess 28 has an end 28b at the first surface 13a, and the second recess 30 has an end 30b at the first surface 13a. A first distance W1 between the end 28b of the first recess 28 and the laser stripe is smaller than a second distance W2 between the end 30b of the second recess 30 and the laser stripe.

The laser structure 13 includes one end 14a, the other end 14b, and an intermediate portion 14c, and the intermediate portion 14c is located between the one end 14a and the other end 14b. In one example of the laser structure 13, the first and second scribed marks are provided at one end and the other end, respectively, of the edge of the first surface 13a at the end 14a. The first and second scribed marks extend along an a-n plane defined by the a-axis of the hexagonal III-nitride semiconductor and the normal axis NX. In the present embodiment, the first and second scribed marks extend from the first surface 13a or epitaxially grown surface toward the back surface 17b of the support base 17. At the end 14a of the laser structure 13, the fractured face 27 is formed so as to connect edges 28e, 30e of the first and second scribed marks and the edges 13c, 13d of the first and second surfaces 13a, 13b of the laser structure 13. For this reason, the laser cavity of the III-nitride semiconductor laser device 11 includes the fractured face 27, and in the laser structure 13, the laser stripe extending in the direction of the waveguide vector LGV above the semipolar principal surface 17a of the support base 17 is provided between the first and second scribed marks at the end 14a. The distance between the end of the first scribed mark and the laser stripe corresponds to the distance represented by reference sign W1 defined for the end 28b of the first recess 28 in the present embodiment. Furthermore, the distance between the end of the second scribed mark and the laser stripe corresponds to the distance represented by reference sign W2 defined for the end 30b of the second recess 30 in the present embodiment. Each of the first and second scribed marks is formed from a scribed groove by fracture, and the scribed groove guides progress of the fracture. Furthermore, the first distance between the laser stripe and the end of the first scribed mark can be made smaller than the second distance between the laser stripe and the end of the second scribed mark, which can reduce the device width WD of the laser device.

In the III-nitride semiconductor laser device 11, the first distance W1 can be not less than 20 μm. In this III-nitride semiconductor laser device, the end 28b of the recess 28 can be located up to the near distance of 20 μm from the laser stripe. The first distance W1 can be less than 50 μm. In this III-nitride semiconductor laser device 11, the first distance W1 is preferably less than 50 μm, for reduction in device width. Furthermore, the first distance W1 may be less than 70 μm.

In the III-nitride semiconductor laser device 11, the first distance W1 can be less than 50 μm, and the second distance W2 not less than 50 μm. In this III-nitride semiconductor laser device 11, the first distance W1 can be made smaller than the second distance W2, which can reduce the device width WD of the laser device.

The width WD of the III-nitride semiconductor laser device 11 can be not more than 200 µm. The III-nitride semiconductor laser device 11 can be provided in the device width of not more than 200 µm.

In the III-nitride semiconductor laser device 11, the first recess 28 includes a slope portion 28c where a bottom 28a of the recess 28 tilts toward the end 28b, and in the slope portion 28c, the depth of the scribed groove becomes shallower, for example, in the positive direction of the Y-axis. The first recess 28 may include a substantially flat portion 28d with a tilt smaller than that of the slope portion 28c, and the flat portion 28d is adjacent to the slope portion 28c. The second recess 30 includes a slope portion 30c where a bottom 30a of the recess 30 tilts toward the end 30b, and in the slope portion 30c, the depth of the scribed groove becomes deeper, for example, in the positive direction of the Y-axis. The second recess 30 may include a substantially flat portion 30d with a tilt smaller than that of the slope portion 30c, and the flat portion 30d is adjacent to this slope portion 30c. The orientation of the tilt at the slope portion 28c of the first recess 28 is opposite to that at the slope portion 30c of the second recess 30. A first length LS1 of the slope portion 28c of the first recess 28 is preferably longer than a second length LS2 of the slope portion 30c of the second recess 30. In this III-nitride semiconductor laser device 11, the scribed grooves are formed so that the first length LS1 is longer than the second length LS2, whereby it is feasible to reduce an adverse effect on laser operation from damage near the end 28b of the first recess 28 with damage greater than that near the end 30b of the second recess 30. For example, a second length LP2 of the flat portion 30c of the second recess 30 can be not less than a first length LP1 of the flat portion 28d of the first recess 28.

The above description concerns the recesses 28, 30 in the fractured face 27. The III-nitride semiconductor laser device 11 may include a fractured face 29 at the end 14b, and the fractured face 29 can include recesses 32, 34. The recesses 32, 34 each can have the same configuration and size as the recesses 28, 30, but do not have to be limited to this.

The electrode 15 is connected through the aperture 31a of the insulating film 31 to the semiconductor region 17 of the laser structure 13. When the III-nitride semiconductor laser device 11 has the gain guiding structure, the first distance W1 can be defined as a distance between the aperture 31a of the insulating film 31 and the end 28b of the first recess 28, and the second distance W2 as a distance between the aperture 31a of the insulating film 31 and the end 30b of the second recess 30. In this III-nitride semiconductor laser device 11, each of the first and second distances W1, W2 can be defined by the distance between the aperture 31a of the insulating film 31 and the end 28b or 30b of the first and second recesses 28, 31. The aperture 31a can have, for example, a stripe shape.

As another example, where the semiconductor region 13 of the laser structure 13 has the ridge structure, the first distance W1 can be defined as a distance between the ridge structure and the end 28b of the first recess 28, and the second distance W2 as a distance between the ridge structure and the end 30b of the second recess 30.

The III-nitride semiconductor laser device 11 includes an n-side light guide layer 35 and a p-side light guide layer 37. The n-side light guide layer 35 includes a first portion 35a and a second portion 35b, and the n-side light guide layer 35 comprises, for example, GaN, InGaN, or the like. The p-side light guide layer 37 includes a first portion 37a and a second portion 37b, and the p-side light guide layer 37 comprises, for example, GaN, InGaN, or the like. A carrier block layer 39 is provided, for example, between the first portion 37a and the second portion 37b. Another electrode 41 is provided on the back surface 17b of the support base 17, and the electrode 41 covers, for example, the back surface 17b of the support base 17.

Figure 3:
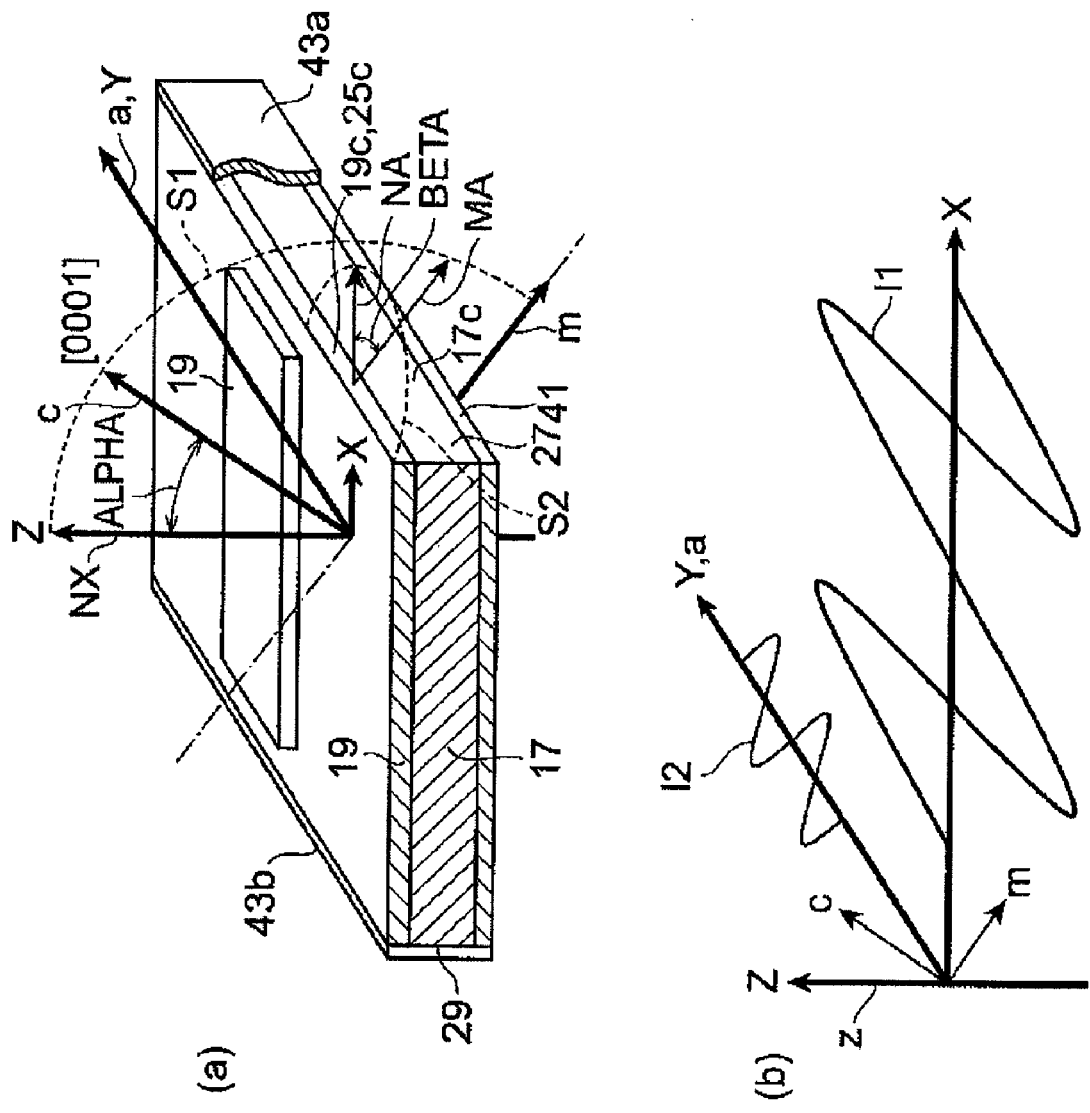
FIG. 3 is a drawing showing polarization of emission in the active layer of the III-nitride semiconductor laser device.
Figure 4:
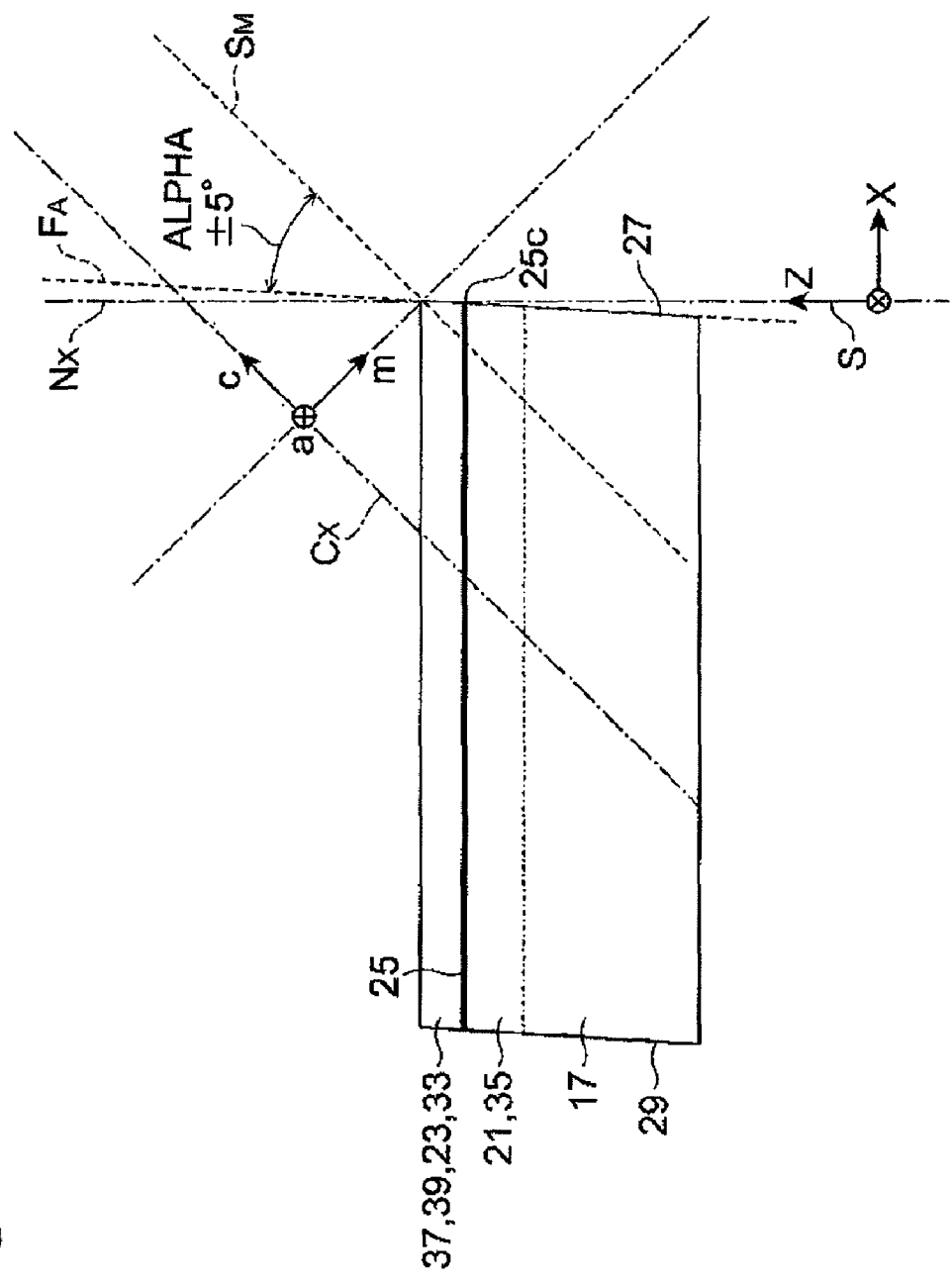
FIG. 4 is a drawing showing a relation between an end face of the III-nitride semiconductor laser device and an m-plane of the active layer.

FIG. 2 is a drawing showing a band structure in the active layer in the III-nitride semiconductor laser device. FIG. 3 is a drawing showing polarization of emission in the active layer 25 of the III-nitride semiconductor laser device 11. FIG. 4 is a drawing schematically showing a cross section defined by the c-axis and the m-axis. With reference to part (a) of FIG. 2, there are three possible transitions between the conduction band and valence bands in the vicinity of Γ point of the band structure BAND. There is a relatively small energy difference between band A and band B. An emission by transition Ea between the conduction band and band A is polarized in the a-axis direction, and an emission by transition Eb between the conduction band and band B is polarized in the projected direction of the c-axis on the principal surface. Concerning laser oscillation, a threshold of transition Ea is smaller than a threshold of transition Eb.

With reference to part (b) of FIG. 2, there are shown spectra of light in the LED mode in the III-nitride semiconductor laser device 11. The light in the LED mode includes a polarization component I1 in the direction of the a-axis of the hexagonal III-nitride semiconductor, and a polarization component I2 in the projected direction of the c-axis of the hexagonal III-nitride semiconductor on the principal surface, and the polarization component I1 is larger than the polarization component I2. Degree of polarization ρ is defined by (I1−I2)/(I1+I2). Using the laser cavity of the III-nitride semiconductor laser device 11, the device can be lased to emit light in a mode with large emission intensity in the LED mode.

As shown in FIG. 3, the device may be further provided with dielectric multilayer film 43a, 43b on at least one of the first and second fractured faces 27, 29 or with both on the respective faces. An end face coat is also applicable to the fractured faces 27, 29. The end face coat allows adjustment of reflectance.

As shown in part (b) of FIG. 3, the laser light L from the active layer 25 is polarized in the direction of the a-axis of the hexagonal III-nitride semiconductor. In this III-nitride semiconductor laser device 11, a band transition allowing for implementation of a low threshold current has polarized nature. The first and second fractured faces 27, 29 for the laser cavity are different from the conventional cleaved facets such as c-planes, m-planes, or a-planes. However, the first and second fractured faces 27, 29 have flatness and perpendicularity enough as mirrors for the cavity. For this reason, by using the first and second fractured faces 27, 29 and the laser waveguide extending between these fractured faces 27, 29, as shown in part (b) of FIG. 3, it becomes feasible to achieve low-threshold laser oscillation through the use of the emission by transition Ea stronger than the emission by transition Eb polarized in the projected direction of the c-axis on the principal surface.

In the III-nitride semiconductor laser device 11, an end face 17c of the support base 17 and an end face 19c of the semiconductor region 19 are exposed in each of the first and second fractured faces 27, 29, and the end face 17c and the end face 19c are covered by the dielectric multilayer film 43a. An angle BETA between a normal vector NA to the end face 17c of the support base 17 and an end face 25c in the active layer 25, and an m-axis vector MA of the active layer 25 is defined by component $(BETA)_1$ defined on a first plane S1 defined by the c-axis and m-axis of the III-nitride semiconductor, and component (BETA)$_2$ defined on a second plane S2 (which is not shown for easier understanding but is referred to as "S2") perpendicular to the first plane S1 (which is not shown for easier understanding but is referred to as "S1") and the normal axis NX. The component (BETA)$_1$ is preferably in a range of not less than (ALPHA−5)° and not more than (ALPHA+5)° on the first plane S1 defined by the c-axis and m-axis of the III-nitride semiconductor. This angle range is shown as an angle between a typical m-plane S$_M$ and a reference plane F$_A$ in FIG. 4. The typical m-plane S$_M$ is depicted from the inside to the outside of the laser structure in FIG. 4, for easier understanding. The reference plane F$_A$ extends along the end face 25c of the active layer 25. This III-nitride semiconductor laser device 11 has the end faces satisfying the aforementioned perpendicularity, as to the angle BETA taken from one to the other of the c-axis and the m-axis. The component (BETA)$_2$ is preferably in a range of not less than −5° and not more than +5° on the second plane S2. Here, BETA$^2$=(BETA)$_1^2$+(BETA)$_2^2$. In this case, the end faces 27, 29 of the III-nitride semiconductor laser device 11 satisfy the aforementioned perpendicularity as to the angle defined on the plane perpendicular to the normal axis NX to the semipolar plane 17a.

Referring again to FIG. 1, in the III-nitride semiconductor laser device 11 the thickness DSUB of the support base 17 is preferably not more than 40 μm. This III-nitride semiconductor laser device is suitable for obtaining good-quality fractured faces for the laser cavity. In the III-nitride semiconductor laser device 11, the thickness DSUB of the support base 17 is more preferably not less than 50 μm and not more than 10 μm. This III-nitride semiconductor laser device 11 is more suitable for obtaining good-quality fractured faces for the laser cavity. Furthermore, handling becomes easier and the production yield becomes higher.

In the III-nitride semiconductor laser device 11, the angle ALPHA between the normal axis NX and the c-axis of the hexagonal III-nitride semiconductor is preferably not less than 45° and preferably not more than 80°. Furthermore, the angle ALPHA is preferably not less than 100° and preferably not more than 135°. When the angle is in a range of less than 45° or in a range of more than 135°, the end faces made by press are highly likely to be comprised of m-planes. When the angle is in a range of more than 80° and less than 100°, it could result in failing to achieve the desired flatness and perpendicularity.

In the III-nitride semiconductor laser device 11, more preferably, the angle ALPHA between the normal axis NX and the c-axis of the hexagonal III-nitride semiconductor is not less than 63° and not more than 80°. Furthermore, the angle ALPHA is more preferably not less than 100° and not more than 117°. When the angle is in a range of less than 63° or in a range of more than 117°, an m-plane can appear in part of an end face made by press. When the angle is in a range of more than 80° and less than 100°, it could result in failing to achieve the desired flatness and perpendicularity.

The semipolar principal surface 17a can be any one of a {20-21} plane, a {10-11} plane, a {20-2-1} plane, and a {10-1-1} plane. Furthermore, a surface with a slight slant in a range of not less than −4° and not more than +4° from these planes is also suitable for the principal surface. On the semipolar surface 17a of one of these typical planes, it is feasible to provide the first and second end faces 27, 29 with flatness and perpendicularity enough to construct the laser cavity of the III-nitride semiconductor laser device 11. Furthermore, the end faces with sufficient flatness and perpendicularity are obtained in an angular range across these typical plane orientations.

In the III-nitride semiconductor laser device 11, the stacking fault density of the support base 17 can be not more than $1 \times 10^4$ cm$^{-1}$. Since the stacking fault density is not more than $1 \times 10^4$ cm$^{-1}$, the flatness and/or perpendicularity of the fractured faces are/is less likely to be disturbed for a certain accidental reason. The support base 17 can comprise any one of GaN, AlN, AlGaN, InGaN, and InAlGaN. When the substrate comprising any one of these GaN-based semiconductors is used, the end faces 27, 29 applicable to the cavity can be obtained. When an AlN or AlGaN substrate is used, it is feasible to increase the degree of polarization and to enhance optical confinement by virtue of low refractive index. When an InGaN substrate is used, it is feasible to decrease the lattice mismatch rate between the substrate and the light emitting layer and to improve crystal quality.

Figure 5:
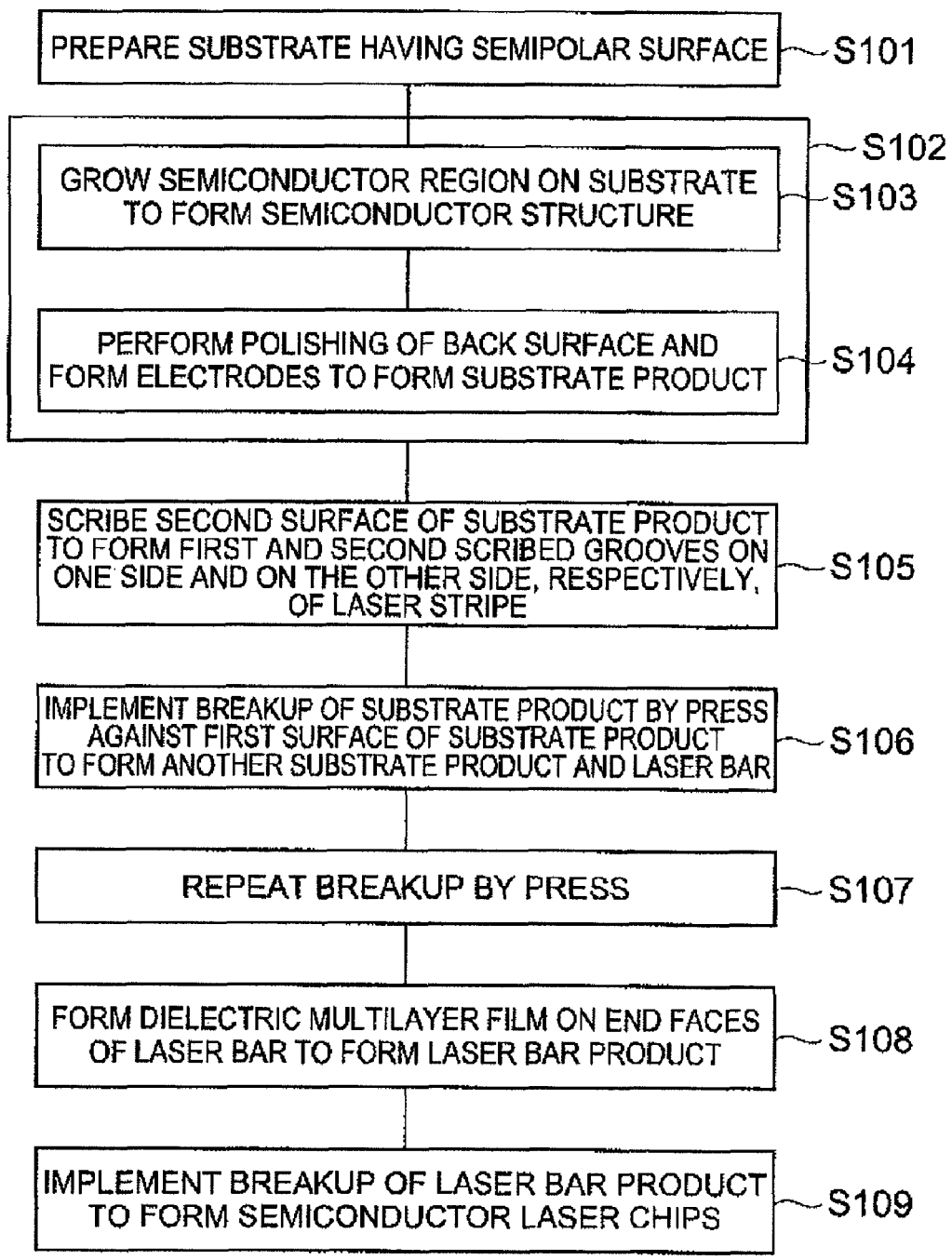
FIG. 5 is a step flowchart showing major steps in a method for fabricating a III-nitride semiconductor laser device according to an embodiment of the present invention.

FIG. 5 is a drawing showing major steps in a method for fabricating a III-nitride semiconductor laser device according to an embodiment of the present invention. With reference to part (a) of FIG. 6, a substrate 51 is shown. Step S101 is to prepare the substrate 51 for fabrication of the III-nitride semiconductor laser device. The c-axis (vector VC) of the hexagonal III-nitride semiconductor of the substrate 51 tilts at the finite angle ALPHA with respect to the normal axis NX toward the m-axis (vector VM) of the hexagonal III-nitride semiconductor. For this reason, the substrate 51 has a semipolar principal surface 51a comprising the hexagonal III-nitride semiconductor.

Step S102 is to form a substrate product SP. In part (a) of FIG. 6, the substrate product SP is depicted as a member of a nearly disklike shape, but the shape of the substrate product SP is not limited to this. For obtaining the substrate product SP, step S103 is first carried out to form a laser structure 55. The laser structure 55 includes a semiconductor region 53 and the substrate 51, and step S103 is to form the semiconductor region 53 on the semipolar principal surface 51a. A first conductivity type GaN-based semiconductor region 57, a light emitting layer 59, and a second conductivity type GaN-based semiconductor region 61 are grown in order on the semipolar principal surface 51a, for forming the semiconductor region 53. The GaN-based semiconductor region 57 can include, for example, an n-type cladding layer, and the GaN-based semiconductor region 61 can include, for example, a p-type cladding layer. The light emitting layer 59 is provided between the GaN-based semiconductor region 57 and the GaN-based semiconductor region 61 and can include an active layer, light guide layers, an electron block layer, and so on. The GaN-based semiconductor region 57, the light emitting layer 59, and the second conductivity type GaN-based semiconductor region 61 are arranged along the normal axis NX to the semipolar principal surface 51a. These semiconductor layers are epitaxially grown. The surface of the semiconductor region 53 is covered by an insulating film 54. The insulating film 54 comprises, for example, silicon oxide. The insulating film 54 has an aperture 54a. The aperture 54a is, for example, a stripe shape.

Step S104 is to form an anode electrode 58a and a cathode electrode 58b on the laser structure 55. Before forming the electrode on the back surface of the substrate 51, the back surface of the substrate used in crystal growth is polished to form a substrate product SP in a desired thickness DSUB. In formation of the electrodes, for example, the anode electrode 58a is formed on the semiconductor region 53, and the cathode electrode 58b is formed on the back surface (polished surface) 51b of the substrate 51. The anode electrode 58a extends in the X-axis direction, and the cathode electrode 58b covers the entire area of the back surface 51b. These steps result in forming the substrate product SP. The substrate product SP includes a first surface 63a, and a second surface 63b located opposite thereto. The semiconductor region 53 is located between the first surface 63a and the substrate 51.

Step S105 is, as shown in part (b) of FIG. 6, to scribe the first surface 63a of the substrate product SP. This scribing step is carried out with a laser scriber 10a. This scribing step results in forming scribed grooves 65a, e.g., in the positive direction of the Y-axis. In part (b) of FIG. 6, five scribed grooves are already formed, and formation of a scribed groove 65b is in progress with a laser beam LB. The length of the scribed grooves 65a is shorter than the length of an intersecting line MS between an a-n plane defined by the a-axis of the hexagonal III-nitride semiconductor and the normal axis NX, and the first surface 63a, and the laser beam LB is applied to a part of the intersecting line MS. By the application with the laser beam LB, grooves extending in the specific direction and reaching the semiconductor region are formed in the first surface 63a. The scribed grooves 65a can be formed, for example, at an edge of the substrate product SP. In an example, the array of scribed grooves are formed by a scan with the laser beam LB along the intersecting line MS.

Specifically, the first surface 63a of the substrate product SP is scribed along a fracture line extending in the direction of the a-axis of the hexagonal III-nitride semiconductor (e.g., the positive direction of the Y-axis) to form first and second scribed grooves 64a, 64b. During the scribing, the laser beam scans in the positive direction of the Y-axis. Therefore, the first scribed groove 64a is first formed and then the second scribed groove 64b is formed. With reference to part (b) of FIG. 6, there is shown a laser stripe extending in the direction of the waveguide axis (X-axis direction). The first scribed groove 64a, the laser stripe LS, and the second scribed groove 64b are arranged in order in the direction of the a-axis of the hexagonal III-nitride semiconductor. In the present embodiment, the laser stripe LS can be defined, for example, by the aperture 54a of the insulating film 54. The first scribed groove 64a has an end 66a at the first surface 63a, and the second scribed groove 64b has an end 66b at the first surface 63a. The first distance W1 between the laser stripe LS and the end 66a of the first scribed groove 64a is smaller than the second distance W2 between the laser stripe LS and the end 66b of the second scribed groove 64b. The first and second scribed grooves 64a, 64b are adjacent to each other, and a distance between the end 66a of the first scribed groove 64a and the end 66b of the second scribed groove 64b is smaller than the width of the III-nitride semiconductor laser device. The end 66a of the first scribed groove 64a is, for example, a terminal end in formation of a scribed groove, and the end 66b of the second scribed groove 64b is, for example, an initial end in formation of a scribed groove. In order to obtain the fractured face in which the extending direction of the scribed grooves (or scribed marks) is described by the depth direction, the scribed groove space (or scribed mark space) is preferably not less than 40 μm and not more than 800 μm.

The first distance W1 can be not less than 20 μm. On the substrate product SP, the size of a damaged region near one end 66a of the scribed groove 64a is smaller than the size of a damaged region near the other end 66b of the scribed groove 64b. The end of the scribed groove with the smaller size of the damaged region can be located up to the minimum distance of about 20 μm from the laser stripe LS. Furthermore, the end of the scribed groove with the larger size of the damaged region can be located up to the minimum distance of about 50 μm from the laser stripe. The first distance W1 can be, for example, less than 50 μm.

The first distance W1 can be less than 50 μm and the second distance W2 not less than 50 μm. Since the adjacent scribed grooves are formed so that the first distance W1 is smaller than the second distance W2, the device width of the laser device can be reduced. This method allows the laser device to be formed in the device width of not more than 200 μm.

Step S106 is, as shown in part (c) of FIG. 6, to implement breakup of the substrate product SP by press against the second surface 63b of the substrate product SP to form a substrate product SP1 and a laser bar LB1. The press is carried out with a breaking device, for example, like a blade 69. The blade 69 includes an edge 69a extending in one direction, and at least two blade faces 69b, 69c defining the edge 69a. The press on the substrate product SP1 is carried out on a support device 70. The support device 70 includes a support table 70a and a recess 70b, and the recess 70b extends in one direction. The recess 70b is formed in the support table 70a. The orientation and position of the scribed groove 65a of the substrate product SP1 are aligned with the extending direction of the recess 70b of the support device 70 to position the substrate product SP1 to the recess 70b on the support device 70. The orientation of the edge of the breaking device is aligned with the extending direction of the recess 70b, and the edge of the breaking device is pressed against the substrate product SP1 from a direction intersecting with the second surface 63b. The intersecting direction is preferably an approximately normal direction to the second surface 63b. This implements the breakup of the substrate product SP to form the substrate product SP1 and laser bar LB1. The press results in forming the laser bar LB1 with first and second end faces 67a, 67b, and these end faces 67a, 67b have perpendicularity and flatness enough to make at least a part of the light emitting layer applicable to the cavity mirrors of the semiconductor laser.

The laser bar LB1 thus formed has the first and second end faces 67a, 67b formed by the aforementioned breakup, and each of the end faces 67a, 67b extends from the first surface 63a to the second surface 63b. For this reason, the end faces 67a, 67b form the laser cavity of the III-nitride semiconductor laser device and intersect with the XZ plane. This XZ plane corresponds to the m-n plane defined by the m-axis of the hexagonal III-nitride semiconductor and the normal axis NX.

According to this method, the first surface 63a of the substrate product SP is scribed in the direction of the a-axis of the hexagonal III-nitride semiconductor and thereafter the breakup of the substrate product SP is carried out by press against the second surface 63b of the substrate product SP, thereby forming the new substrate product SP1 and the laser bar LB1. For this reason, the first and second end faces 67a, 67b are formed in the laser bar LB1 so as to intersect with the m-n plane. This end face forming method provides the first and second end faces 67a, 67b with flatness and perpendicularity enough to construct the laser cavity of the III-nitride semiconductor laser device.

In this method, the laser waveguide formed extends in the direction of tilt of the c-axis of the hexagonal III-nitride. The cavity mirror end faces allowing for provision of this laser waveguide are formed without use of dry-etched facets. In this method, when the angle is in a range of less than 45° or in a range of more than 135°, end faces made by press are highly likely to be comprised of m-planes. When the angle is in a range of more than 80° and less than 100°, it might result in failing to achieve the desired flatness and perpendicularity.

This method involves the fracture of the substrate product SP1, thereby forming the new substrate product SP1 and the laser bar LB1. Step S107 is to repeatedly carry out the breakup by press to produce many laser bars. This fracture is brought about using the scribed groove 65a shorter than a fracture line BREAK of the laser bar LB1.

In this method, the scribed grooves 64a, 64b and laser stripes LS are alternately arranged in the a-axis direction on the substrate product SP1. A scribed groove is formed between two adjacent laser stripes. Damage caused by formation of the scribed grooves is not isotropic in the vicinity of the scribed grooves 64a, 64b. Namely, damaged regions due to formation of the scribed grooves 64a, 64b are formed in asymmetry around the scribed grooves. For this reason, the size of the damaged region near one end 66a of the scribed groove 64a is smaller than the size of the damaged region near the other end 66b of the scribed groove 64b. When attention is focused on one laser stripe among the array of laser stripes LS, the first distance (distance between the laser stripe LS and the end 66a of the first scribed groove 64a as shown in part (b) of FIG. 6) W1 can be made smaller than the second distance (distance between the laser stripe LS and the end 66b of the second scribed groove 64b) W2. Therefore, the device width of the laser device can be reduced.

Step S108 is to form dielectric multilayer films on the end faces 67a, 67b of the laser bar LB1 to form a laser bar product. Step S109 is to break this laser bar product into chips of individual semiconductor lasers.

In the fabrication method according to the present embodiment, the angle ALPHA can be in a range of not less than 45° and not more than 80° or in a range of not less than 100° and not more than 135°. When the angle is in a range of less than 45° or in a range of more than 135°, the end face made by press becomes highly likely to be comprised of an m-plane. When the angle is in a range of more than 80° and less than 100°, it could result in failing to achieve desired flatness and perpendicularity. More preferably, the angle ALPHA can be in a range of not less than 63° and not more than 80° or in a range of not less than 100° and not more than 117°. When the angle is in a range of less than 45° or in a range of more than 135°, an m-plane can appear in part of an end face formed by press. When the angle is in a range of more than 80° and less than 100°, it could result in failing to achieve the desired flatness and perpendicularity. The semipolar principal surface 51a can be any one of a {20-21} plane, a {10-11} plane, a {20-2-1} plane, and a {10-1-1} plane. Furthermore, a surface with a slight slant in a range of not less than −4° and not more than +4° from these planes is also suitable for the principal surface. On these typical semipolar planes, it is feasible to provide the end faces for the laser cavity with flatness and perpendicularity enough to construct the laser cavity of the III-nitride semiconductor laser device.

The substrate 51 can comprise any one of GaN, AlN, AlGaN, InGaN, and InAlGaN. When the substrate used comprises any one of these GaN-based semiconductors, it is feasible to obtain the end faces applicable to the laser cavity. The substrate 51 preferably comprises GaN.

In the step S104 of forming the substrate product SP, the semiconductor substrate used in crystal growth can be one subjected to processing such as slicing or grinding so that the substrate thickness becomes not more than 400 μm, and having the second surface 63b of a processed surface formed by polishing. In this substrate thickness, the end faces 67a, 67b can be formed in good yield, with flatness and perpendicularity enough to construct the laser cavity of the III-nitride semiconductor laser device or without ion damage. More preferably, the second surface 63b is a polished surface formed by polishing, and the substrate thickness after polishing is not more than 100 μm. For relatively easily handling the substrate product SP, the substrate thickness is preferably not less than 50 μm.

In the production method of the laser end faces according to the present embodiment, the angle BETA explained with reference to FIG. 3 is also defined in the laser bar LB1. In the laser bar LB1, the component $(BETA)_1$ of the angle BETA is preferably in a range of not less than (ALPHA−5)° and not more than (ALPHA+5)° on a first plane (plane corresponding to the first plane S1 in the description with reference to FIG. 3) defined by the c-axis and m-axis of the III-nitride semiconductor. The end faces 67a, 67b of the laser bar LB1 satisfy the aforementioned perpendicularity as to the angle component of the angle BETA taken from one to the other of the c-axis and the m-axis. The component $(BETA)_2$ of the angle BETA is preferably in a range of not less than −5° and not more than +5° on a second plane (plane corresponding to the second plane S2 shown in FIG. 3). In this case, the end faces 67a, 67b of the laser bar LB1 satisfy the aforementioned perpendicularity as to the angle component of the angle BETA defined on the plane perpendicular to the normal axis NX to the semipolar plane 51a.

The end faces 67a, 67b are formed by break by press against the plurality of GaN-based semiconductor layers epitaxially grown on the semipolar plane 51a. Since they are epitaxial films on the semipolar plane 51a, the end faces 67a, 67b are not cleaved facets with a low plane index like c-planes m-planes, or a-planes which have been used heretofore for the conventional cavity mirrors. However, through the break of the stack of epitaxial films on the semipolar plane 51a, the end faces 67a, 67b have the flatness and perpendicularity applicable as cavity mirrors.

EXAMPLE 1

A semipolar-plane GaN substrate is prepared, and perpendicularity of a fractured face is observed as described below. The substrate used is a {20-21}-plane GaN substrate cut at the angle of 75° toward the m-axis out of a (0001) GaN ingot thickly grown by HYPE. The principal surface of the GaN substrate is mirror-finished, and the back surface is in a ground pear-skin state. The thickness of the substrate is 370 μm.

On the back side in the pear-skin state, a marking line is drawn perpendicularly to the projected direction of the c-axis on the principal surface of the substrate, with a diamond pen, and thereafter the substrate is fractured by press. For observing the perpendicularity of the resultant fractured face, the substrate is observed from the a-plane direction with a scanning electron microscope.

Part (a) of FIG. 7 is a scanning electron microscope image of the fractured face observed from the a-plane direction, and the right end face is the fractured face. It is seen that the fractured face has flatness and perpendicularity to the semipolar principal surface.

EXAMPLE 2

Figure 8:
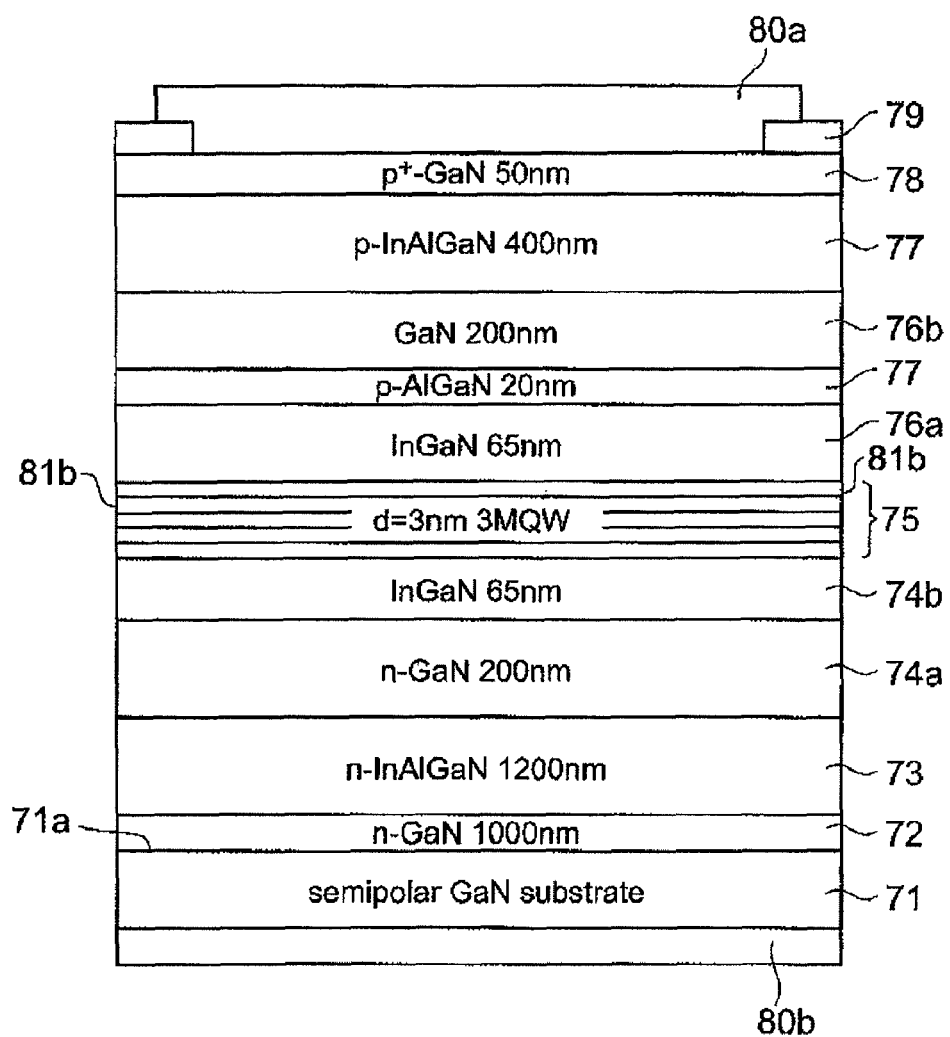
FIG. 8 is a drawing showing a structure of a laser diode shown in Example 1.

It is found in Example 1 that in the GaN substrate having the semipolar {20-21} plane, the fractured face obtained by drawing the marking line perpendicular to the projected direction of the c-axis on the principal surface of the substrate and pressing the substrate has the flatness and perpendicularity to the principal surface of the substrate. For checking applicability of this fractured face to the laser cavity, a laser diode shown in FIG. 8 is grown by metal-organic vapor phase epitaxy as described below. The raw materials used are trimethyl gallium (TMGa), trimethyl aluminum (TMAl), trimethyl indium (TMIn), ammonia ($NH_3$), and silane ($SiH_4$). A substrate 71 is prepared. The substrate 71 prepared is a GaN substrate cut at an angle in a range of 0° to 90° toward the m-axis out of a (0001) GaN ingot thickly grown by HVPE, with a wafer slicing device, in such a manner that the angle ALPHA of tilt of the c-axis toward the m-axis has a desired off angle in a range of 0° to 90°. For example, when the substrate is cut at the angle of 75°, the resultant substrate is a {20-21}-plane GaN substrate, and it is represented by reference symbol 71a in the hexagonal crystal lattice shown in part (b) of FIG. 7.

Before the growth, the substrate is observed by the cathodoluminescence method in order to check the stacking fault density of the substrate. The cathodoluminescence is to observe an emission process of carriers excited by an electron beam, and if there is a stacking fault, non-radiative recombination of carriers occurs in the vicinity thereof to be observed as a dark line. The stacking fault density is defined as a density (line density) per unit length of dark lines. The cathodoluminescence method of nondestructive measurement is applied herein in order to check the stacking fault density, but it is also possible to use a transmission electron microscope of destructive measurement. When a cross section of a sample is observed from the a-axis direction with the transmission electron microscope, a defect extending in the m-axis direction from the substrate toward the sample surface is a stacking fault included in the support base, and the line density of stacking faults can be determined in the same manner as in the case of the cathodoluminescence method.

This substrate 71 is placed on a susceptor in a reaction furnace, and the epitaxial layers are grown according to the following growth procedure. First, n-type GaN 72 is grown in the thickness of 1000 nm. Next, an n-type InAlGaN cladding layer 73 is grown in the thickness of 1200 nm. Thereafter, an n-type GaN guide layer 74a and an undoped InGaN guide layer 74b are grown in the thickness of 200 nm and in the thickness of 65 nm, respectively, and then a three-cycle MQW 75 comprising GaN 15 nm thick/InGaN 3 nm thick is grown. Subsequently grown are an undoped InGaN guide layer 76a in the thickness of 65 nm, a p-type AlGaN block layer 77 in the thickness of 20 nm, and a p-type GaN guide layer 76b in the thickness of 200 nm. Then a p-type InAlGaN cladding layer 77 is grown in the thickness of 400 nm. Finally, a p-type GaN contact layer 78 is grown in the thickness of 50 nm.

An insulating film 79 of $SiO_2$ is deposited on the contact layer 78, and then photolithography is used to form a stripe window in the width of 10 μm by wet etching. In this step, two types of contact windows are formed along two stripe directions. They are the laser stripe along (1) M-direction (direction of the contact window extending along the predetermined plane defined by the c-axis and the m-axis), and the laser stripe along (2) A-direction: <11-20> direction.

After the formation of the stripe window, a p-side electrode 80a of Ni/Au, and a pad electrode of Ti/Al are made by vapor deposition. Next, the back surface of the GaN substrate (GaN wafer) is polished using a diamond slurry to produce a substrate product with the back surface in a mirror state. At this time, the thickness of the substrate product is measured with a contact film thickness meter. The measurement of thickness may also be carried out from a sample cross section with a microscope. The microscope applicable herein is an optical microscope or a scanning electron microscope. An n-side electrode 80b of Ti/Al/Ti/Au is formed by vapor deposition on the back surface (polished surface) of the GaN substrate (GaN wafer).

The cavity mirrors for these two types of laser stripes are produced with a laser scriber using the YAG laser at the wavelength of 355 nm. When the break is implemented with the laser scriber, the lasing chip yield can be improved as compared with the case using the diamond scribing method. The conditions for formation of the scribed grooves are as follows: laser beam output of 100 mW; scanning speed of 5 mm/s. The scribed grooves thus formed are, for example, grooves having the length of 30 μm, the width of 10 μm, and the depth of 40 μm. The scribed grooves are formed by applying the laser beam directly to the epitaxially grown surface at the pitch of 800 μm and through the aperture of the insulating film of the substrate. The cavity length is 600 μm.

The cavity mirrors are made by fracture using a blade. A laser bar is produced by break by press against the back side of the substrate. More specifically, part (b) of FIG. 7 and part (c) of FIG. 7 show relations between crystal orientations and fractured faces, for the {20-21}-plane GaN substrate. Part (b) of FIG. 7 shows the case where the laser stripe is provided (1) in the M-direction and shows end faces 81a, 81b for the laser cavity along with the semipolar plane 71a. The end faces 81a, 81b are approximately perpendicular to the semipolar plane 71a, but are different from the conventional cleaved facets such as the hitherto-used c-planes, m-planes, or a-planes. Part (c) of FIG. 7 shows the case where the laser stripe is provided (2) in the <11-20> direction and shows end faces 81c, 81d for the laser cavity along with the semipolar plane 71a. The end faces 81c, 81d are approximately perpendicular to the semipolar plane 71a and are composed of a-planes.

The fractured faces made by the break are observed with a scanning electron microscope and no prominent unevenness is observed in each of (1) and (2). From this result, the flatness (magnitude of unevenness) of the fractured faces is believed to be not more than 20 nm. Furthermore, the perpendicularity of the fractured faces to the surface of the sample is within a range of ±5°.

The end faces of the laser bar are coated with a dielectric multilayer film by vacuum vapor deposition. The dielectric multilayer film comprises an alternate stack of $SiO_2$ and $TiO_2$. The thickness of each layer is adjusted in a range of 50 to 100 nm, and is designed so that the center wavelength of reflectance falls within a range of 500 to 530 nm. The reflecting surface on one side has ten cycles and the designed value of reflectance of about 95%, and the reflecting surface on the other side has six cycles and the designed value of reflectance of about 80%.

Evaluation by energization is carried out at room temperature. A power supply used is a pulsed power source with the pulse width of 500 ns and the duty ratio of 0.1%, and the energization is implemented with needles on the surface electrodes. On the occasion of light output measurement, the emission from the laser bar end face is detected with a photodiode to check the current-light output characteristic (I-L characteristic). In measurement of emission wavelength, the emission from the laser bar end face is made to pass through an optical fiber, and a spectrum thereof is measured with a spectrum analyzer as a detector. In checking a polarization state, the emission from the laser bar is made to pass through a polarizing plate to rotate, thereby checking the polarization state. In observation of LED-mode emission, an optical fiber is arranged on the front surface side of the laser bar to measure light emitted from the front surface.

The polarization state after oscillation is checked for every laser, and it is found that the light is polarized in the a-axis direction. The lasing wavelength is 500-530 nm.

The polarization state in the LED mode (spontaneous emission) is measured for every laser. When the polarization component in the a-axis direction is I1 and the polarization component in the projected direction of the m-axis on the principal surface is I2, the polarization degree ρ is defined as (I1−I2)/(I1+I2). In this way, the relation between determined polarization degree ρ and minimum of threshold current density is investigated, and the result obtained is as shown in FIG.

9. It is seen from FIG. 9 that the threshold current density demonstrates a significant decrease in the case of the laser (1) with the laser stripe along the M-direction when the polarization degree is positive. Namely, it is seen that when the polarization degree is positive (I1>I2) and when the waveguide is provided along an off direction, the threshold current density is significantly decreased.

Figure 9:
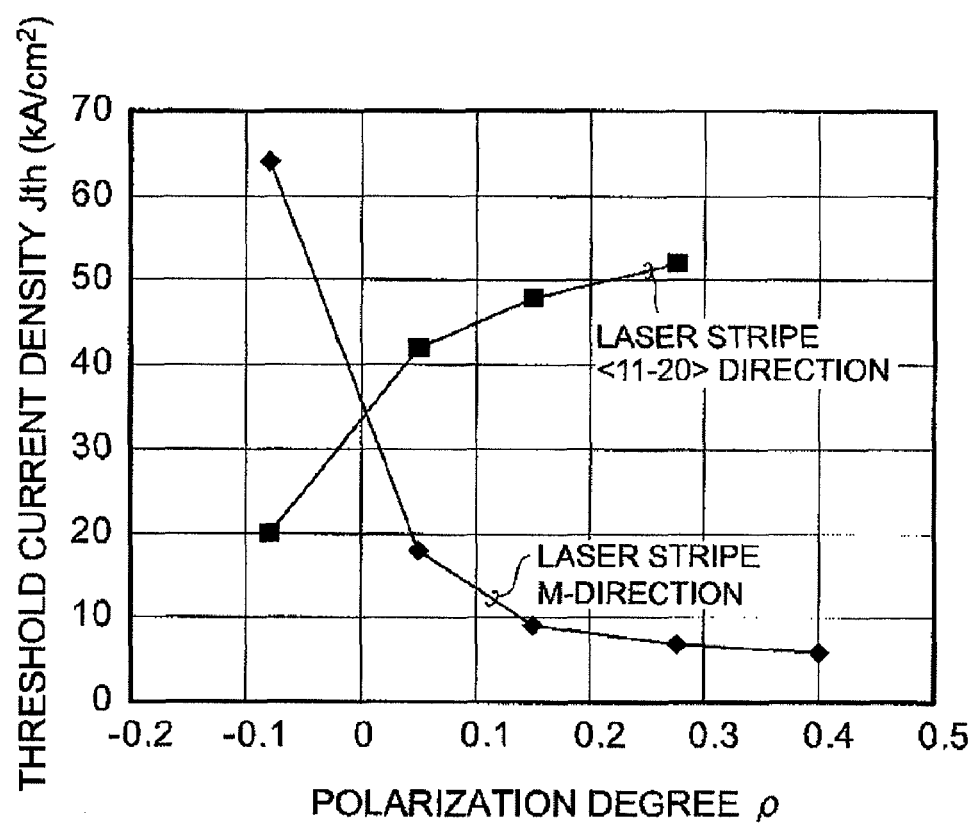
FIG. 9 is a drawing showing a relation of determined polarization degree ρ versus threshold current density.

The data shown in FIG. 9 is as described below.

| polarization degree, | threshold current (M-direction stripe), | threshold current (<11-20> stripe), |
|---|---|---|
| 0.08, | 64, | 20, |
| 0.05, | 18, | 42, |
| 0.15, | 9, | 48, |
| 0.276, | 7, | 52, |
| 0.4, | 6 | |

Figure 10:
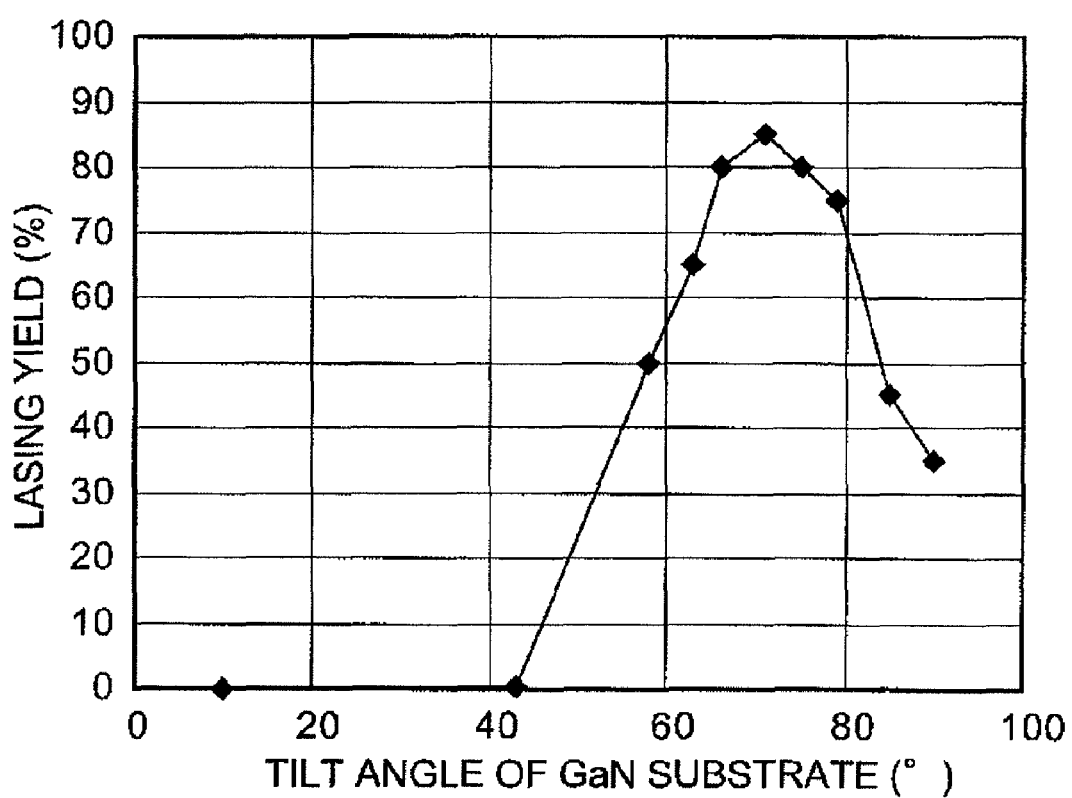
FIG. 10 is a drawing showing a relation of tilt angle of the c-axis toward the m-axis of GaN substrate versus lasing yield.

The relation between the tilt angle of the c-axis of the GaN substrate toward the m-axis and lasing yield is investigated, and the result obtained is as shown in FIG. 10. In the present example, the lasing yield is defined as (the number of lasing chips)/(the number of measured chips). FIG. 10 is a plot for substrates with the stacking fault density of substrate of not more than $1\times10^4$ (cm$^{-1}$) and lasers with the laser stripe along (1) the M-direction. It is seen from FIG. 10 that the lasing yield is extremely low with the off angles of not more than 45°. The end face state is observed with an optical microscope, and it is found that an m-plane appeared in almost all chips, at angles smaller than 45°, resulting in failure in achieving perpendicularity. It is also seen that when the off angle is in a range of not less than 63° and not more than 80°, the perpendicularity is improved, and the lasing yield increases to 50% or more. From these facts, the optimum range of off angle of the GaN substrate is not less than 63° and not more than 80°. The same result is also obtained in a range of not less than 100° and not more than 117°, which is an angular range to provide crystallographically equivalent end faces.

The data shown in FIG. 10 is as described below.

| tilt angle, | yield, |
|---|---|
| 10, | 0.1, |
| 43, | 0.2, |
| 58, | 50, |
| 63, | 65, |
| 66, | 80, |
| 71, | 85, |
| 75, | 80, |
| 79, | 75, |
| 85, | 45, |
| 90, | 35 |

Figure 11:
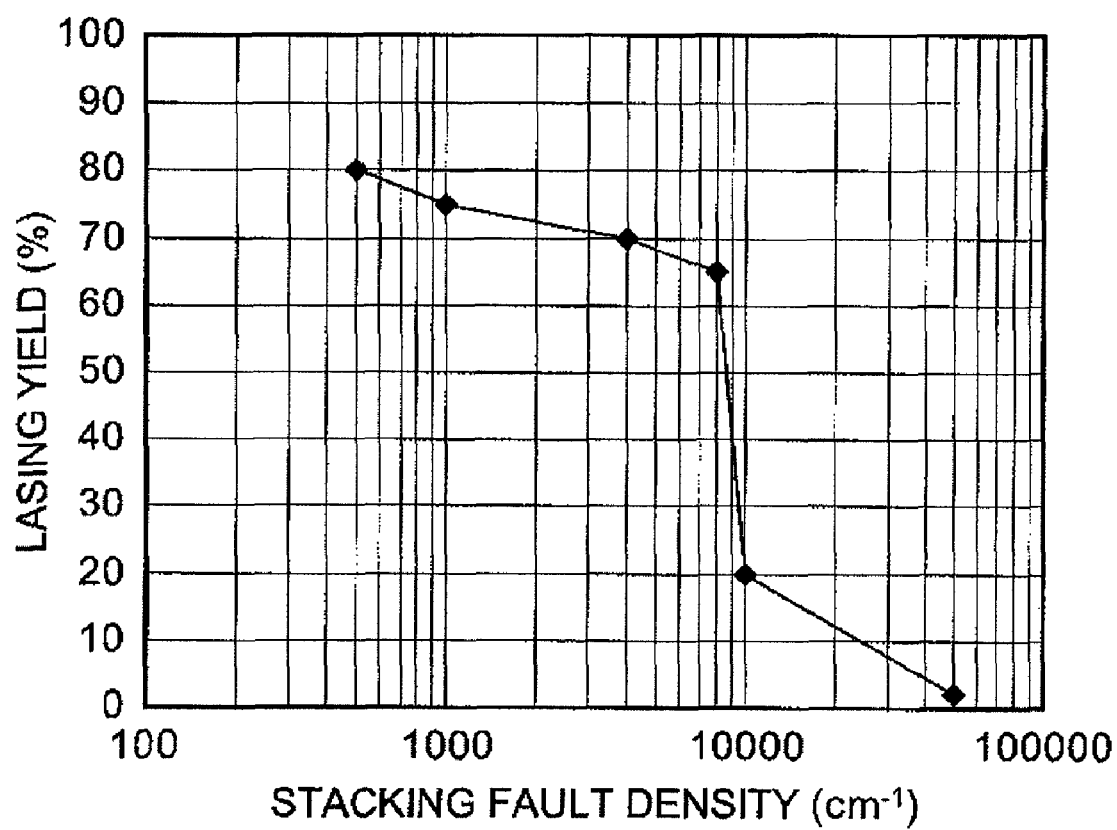
FIG. 11 is a drawing showing a relation of stacking fault density versus lasing yield.

The relation between stacking fault density and lasing yield is investigated, and the result obtained is as shown in FIG. 11. The definition of lasing yield is the same as above. It is seen from FIG. 11 that the lasing yield is suddenly decreased with the stacking fault density over $1\times10^4$ (cm$^{-1}$). When the end face state is observed with an optical microscope, it is found that with samples having the decreased lasing yield, the unevenness of the end faces is significant, and no flat fractured faces are obtained. A conceivable reason is that there is a difference in easiness of fracture because of the existence of stacking faults. From this result, the stacking fault density in the substrate needs to be not more than $1\times10^4$ (cm$^{-1}$).

The data shown in FIG. 11 is as described below.

| stacking fault density (cm$^{-1}$), | yield, |
|---|---|
| 500, | 80, |
| 1000, | 75, |
| 4000, | 70, |
| 8000, | 65, |
| 10000, | 20, |
| 50000, | 2 |

Figure 12:
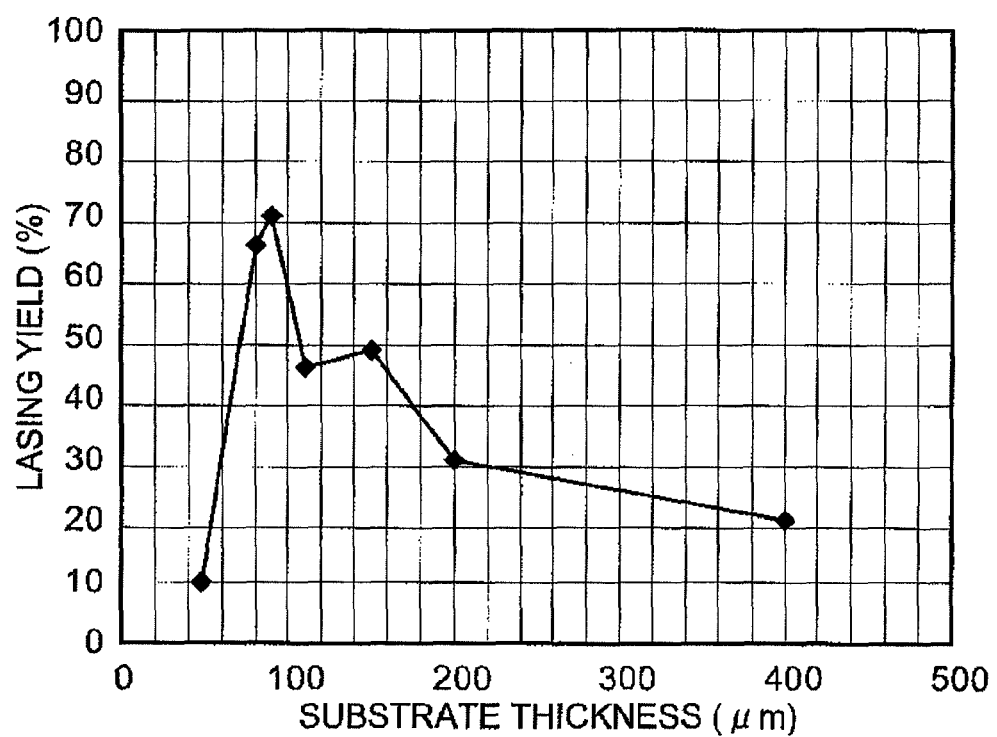
FIG. 12 is a drawing showing a relation of substrate thickness versus lasing yield.

The relation between substrate thickness and lasing yield is investigated, and the result obtained is as shown in FIG. 12. The definition of lasing yield is the same as above. FIG. 12 is a plot for lasers in which the stacking fault density of the substrate is not more than $1\times10^4$ (cm$^{-1}$) and in which the laser stripe extends along (1) the M-direction. From FIG. 12, the lasing yield is high when the substrate thickness is not more than 100 μm and not less than 50 μm. This is because the perpendicularity of fractured faces becomes deteriorated when the substrate thickness is larger than 100 μm. It is also because handling becomes difficult and a chip becomes easy to break when the thickness is smaller than 50 μm. From these, the optimum thickness of the substrate is not less than 50 μm and not more than 100 μm.

The data shown in FIG. 12 is as described below.

| substrate thickness, | yield, |
|---|---|
| 48, | 10, |
| 80, | 65, |
| 90, | 70, |
| 110, | 45, |
| 150, | 48, |
| 200, | 30, |
| 400, | 20 |

EXAMPLE 3

The substrate used is a {20-21}-plane GaN substrate grown by HVPE, and an n-type GaN layer is grown in the thickness of 1000 nm on this GaN substrate. A scribed groove is formed in the GaN-based semiconductor grown in this way, by laser scribing. The size of a damaged region formed around the scribed groove is investigated. The scribed groove is formed with a laser scriber using the YAG laser at the wavelength of 355 nm. The processing conditions are as follows. Laser beam output 100 mw; scanning speed 5 mm/s. The scribed groove thus formed is a groove having approximately the length of 200 μm, the width of 10 μm, and the depth of 40 μm.

In the present example, the damaged region is evaluated by the cathodoluminescence method. The cathodoluminescence is to observe an emission process of carriers excited with an electron beam. However, if processing damage or the like is introduced by formation of the scribed groove, non-radiative recombination centers are formed near the region where the scribed groove is formed. For this reason, carriers undergo non-radiative recombination in the damaged region, and therefore the damaged region is observed as a dark region. Since the diffusion length of carriers in GaN is about 0.1 μm, the damaged region of several μm order can be observed.

Figure 13:
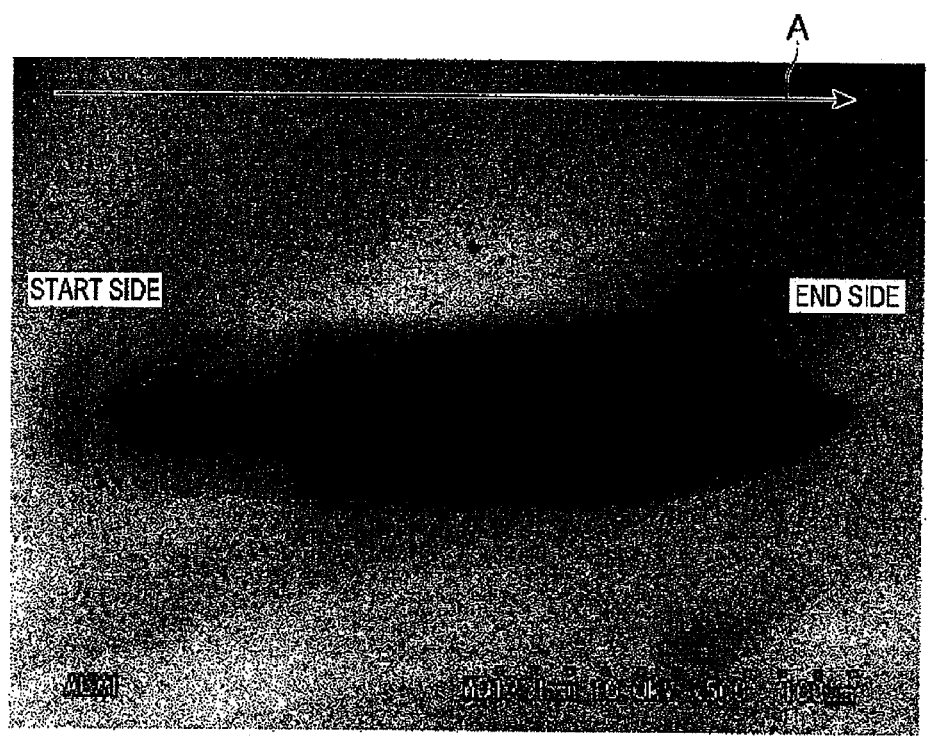
FIG. 13 is a drawing showing an example of a cathodoluminescence (CL) image of a region around a scribed groove.
Figure 14:
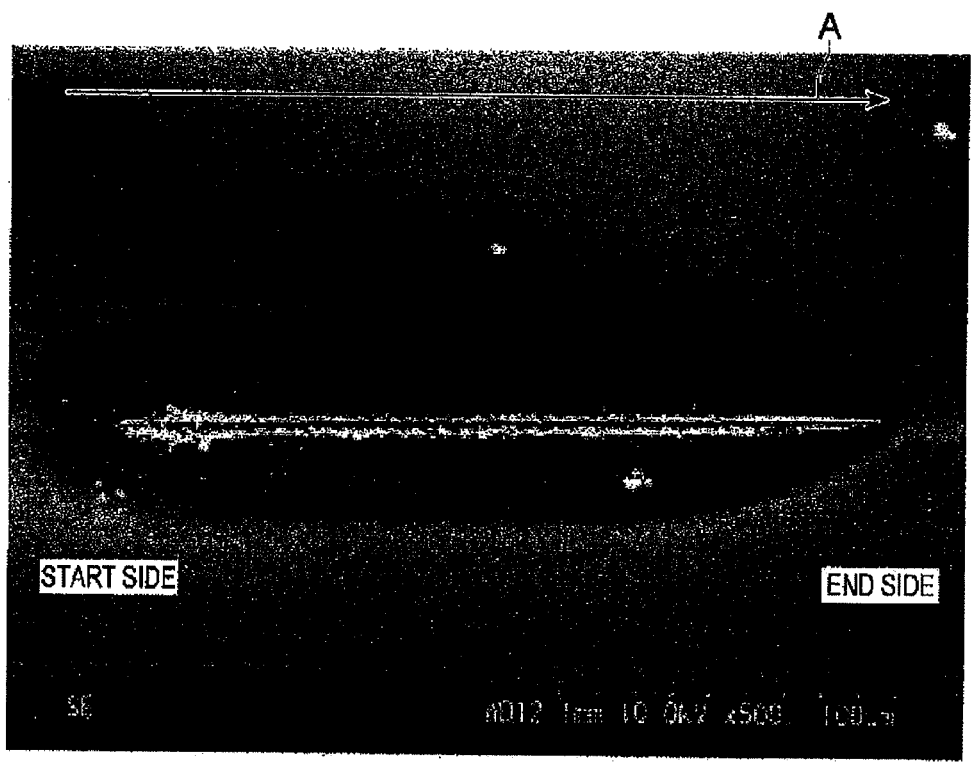
FIG. 14 is a drawing showing an example of a secondary electron emission (SE) image of a region around a scribed groove.

Since an increase in acceleration voltage results in increasing information about the interior of crystal, the observation is carried out using a relatively low acceleration voltage of not more than 10 kV to observe a surface layer region of not more than 0.5 μm from the surface, whereby an abnormal region with great damage can be discriminated from a normal region. FIG. 13 shows an example of a cathodoluminescence (CL) image showing the region around the scribed groove. FIG. 14 is an example of a scanning electron microscope (SEM) image showing the region around the scribed groove. Dark and light regions are observed near the scribed groove, not only in the CL image but also in the SEM image.

The scribed groove shown in FIGS. 13 and 14 is formed by a scan in a direction of arrow A with a laser beam. The laser scans from the left end in these drawings to start forming the scribed groove, and the laser irradiation is terminated at the right end. In a certain period (initial period) from the time of the start, the laser power is continuously increased. In a period (end period) from a time a little before the end to the time of the end, the laser power is continuously decreased. In a period between the initial period and the end period, the laser power is not intentionally changed. By this laser power control, the groove is formed in the shape shown in the cross-sectional image of FIG. 15 (e.g., the shape of a ship bottom). The groove shape shown in FIG. 15 enables formation of the fractured face suitable for the cavity. The cross-sectional shape of the scribed groove has the bottom shape of a boat (ship).

Figure 15:
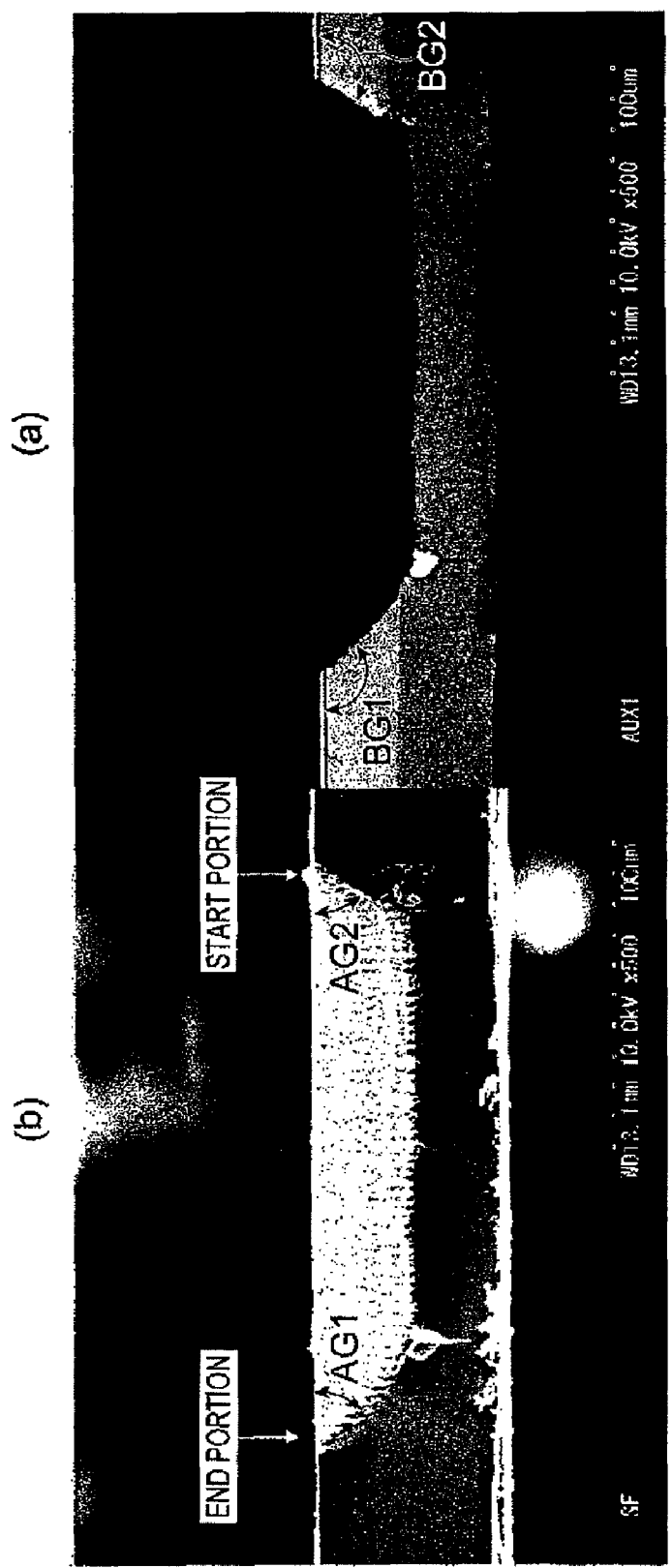
FIG. 15 is a drawing showing (a) an SE image and (b) a CL image of a cross section of a scribed groove.

It is shown in the cross-sectional image of FIG. 15 that the scribed groove and scribed mark include a first slope portion formed in the end period of the scribing, a second slope portion formed in the initial period of the scribing, and a flat portion between the first slope portion and the second slope portion. The length of the second slope portion (initial end) is shorter than the length of the first slope portion (terminal end). The tilt of the bottom in the first slope portion (terminal end) is gentler than the tilt of the bottom in the second slope portion (initial end). A tilt angle AG2 between a straight line connecting a start point and an end point in the second slope portion (initial end) and a straight line extending along the epitaxially grown surface is larger than a tilt angle AG1 between a straight line connecting a start point and an end point in the first slope portion (terminal end) and the straight line extending along the epitaxially grown surface. An angle BG2 between the straight line connecting the start point and the end point in the second slope portion (initial end) and the epitaxially grown surface is smaller than an angle BG1 between the straight line connecting the start point and the end point in the first slope portion (terminal end) and the epitaxially grown surface.

Part (a) of FIG. 15 shows the CL image of the scribed mark remaining near the edge of the fractured face. The CL image is the result of observation of an emission image, and the dark-contrast region in the CL image includes a large number of non-radiative centers formed by the laser irradiation. Part (b) of FIG. 15 shows the SEM image of the scribed mark remaining near the edge of the fractured face. The SEM image is the result of observation of an image by secondary electrons, and the dark region in the SEM image includes a large number of altered portions made by the laser irradiation.

Referring again to FIGS. 13 and 14, the length of the scribed groove is 200 μm with reference to the SEM image. With reference to the CL image, the emission is weak in a region of about 30 μm from the start portion of the scribed groove, and this indicates that damage is introduced to this region. On the other hand, in the end portion of the scribed groove, the damaged region in the CL image is approximately the same as the terminal end position of the scribed groove, and this indicates that the damaged region is not more than several μm of the end portion. It is shown with reference to the SEM image that a large number of debris (deposits made by ablation) exist in the damaged region. However, there is few debris on the right side of the terminal end of the scribed groove. This suggests that the end portion of laser irradiation may be closer than 70 μm to the waveguide, without degradation of the laser characteristic. More specifically, the end of the scribed groove can be located close to the laser stripe in a range of not less than 20 μm and less than 70 μm. This allows the gap between scribed grooves to be decreased. Since the decrease in the gap between scribed grooves allows improvement in perpendicularity upon fracture and decrease in chip width, it can increase the number of chips taken out of one wafer. Therefore, it is feasible to increase the yield in formation of the fractured face and increase the number of chips taken. As a result of this, it is feasible to decrease production cost.

Since the evaluation is conducted by the cathodoluminescence method as described above, the cathodoluminescence allows observation of the emission process of carriers excited with an electron beam. When processing damage or the like is introduced during formation of the scribed groove, carriers undergo non-radiative recombination in the vicinity of the damaged region. Because of the carrier recombination at non-radiative centers, the damaged region is observed as a dark region. Since the diffusion length of carriers in GaN is about 0.1 μm, it is feasible to observe the damaged region of several μm order. The depth of observation is preferably deeper than the scribed groove, but increase in acceleration voltage results in increasing information about the interior of crystal. Therefore, the observation is preferably carried out using a relatively low acceleration voltage of about not more than 10 kV and not less than 3 kV. The use of such acceleration voltage allows the information about carrier recombination centers from the surface layer to be obtained as a visual image.

From the above description, an estimation can be made about a level of damage around a groove by making use of the method for evaluating the damage caused by formation of the scribed groove. By this method, there appears a difference according to damage due to formation of the scribed groove in the image of the region near the groove, which is obtained with a scanning electron microscope, a cathodoluminescence measuring device, or the like. The estimation can be made about the level of damage to an adjacent region to the groove, based on the image with the scanning electron microscope or the cathodoluminescence measuring device.

Figure 16:
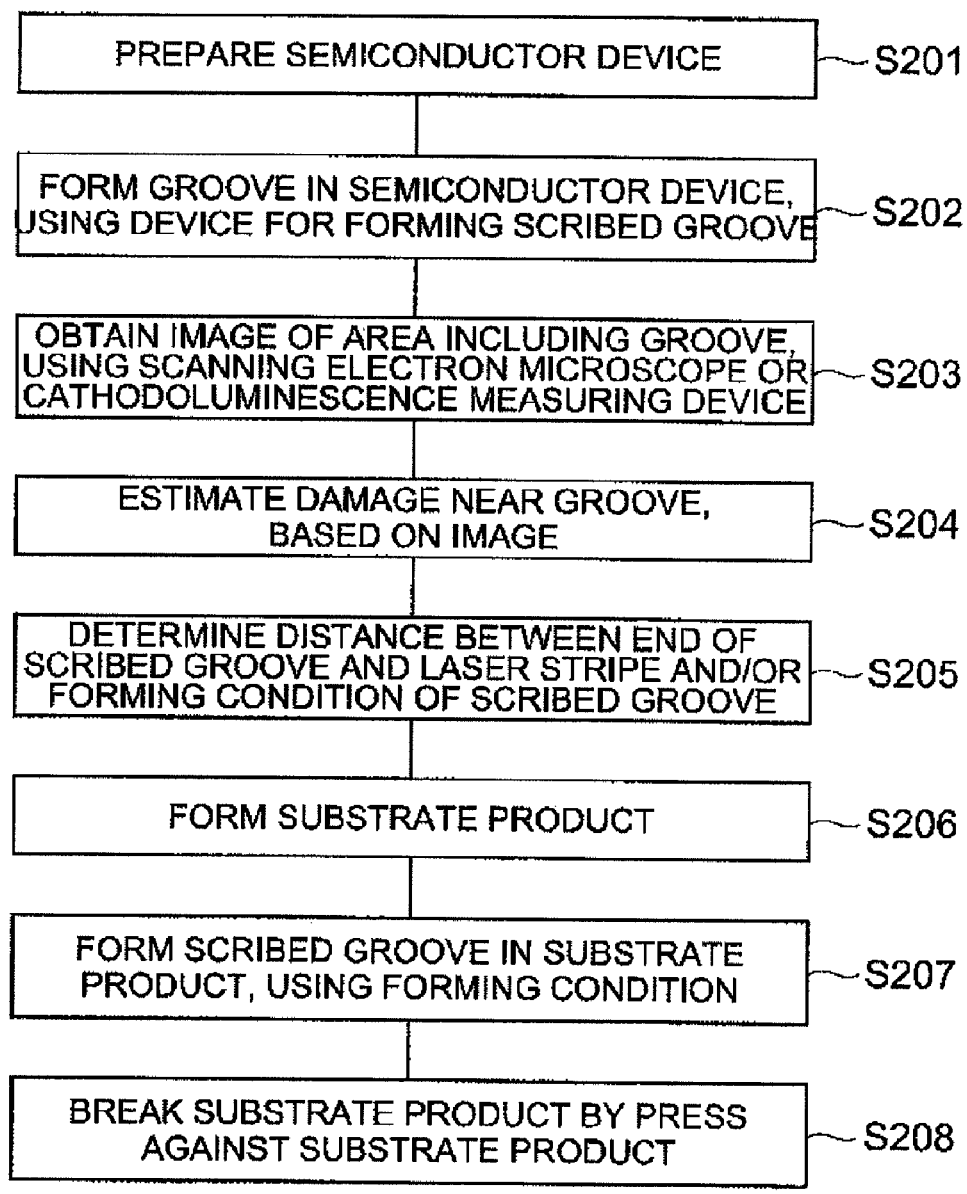
FIG. 16 is a drawing showing major steps in a method for evaluating damage.

The method for evaluating the damage can include, for example, the following steps shown in FIG. 16. Step S201 is to prepare a semiconductor device to be subjected to processing of a groove. The semiconductor device can include a substrate comprising a hexagonal III-nitride semiconductor and a hexagonal III-nitride semiconductor region formed on the substrate, or can include a substrate comprising a hexagonal III-nitride semiconductor. Step S202 is to form a groove in the semiconductor device including the hexagonal III-nitride semiconductor, using a device for forming a scribed groove. Step S203 is to obtain an image of an area including the groove of the semiconductor device, using either of the scanning electron microscope and the cathodoluminescence measuring device for the semiconductor device, after the formation of the groove. Step S204 is to make an estimation about a level of damage to the area near the groove, based on the image. Step S205 is to determine the distance between the end of the scribed groove and the laser stripe of the semiconductor laser and/or a forming condition of the scribed groove. Step S206 is to form a substrate product for III-nitride semiconductor laser device. Step S207 is to form the scribed groove in the substrate product, using the determined forming condition and groove distance. Step S208 is to perform breakup of the substrate product by press on the substrate product, after the formation of scribed groove in the substrate product. This breakup results in, for example, obtaining a laser bar and/or a laser chip.

EXAMPLE 4

Figure 18:
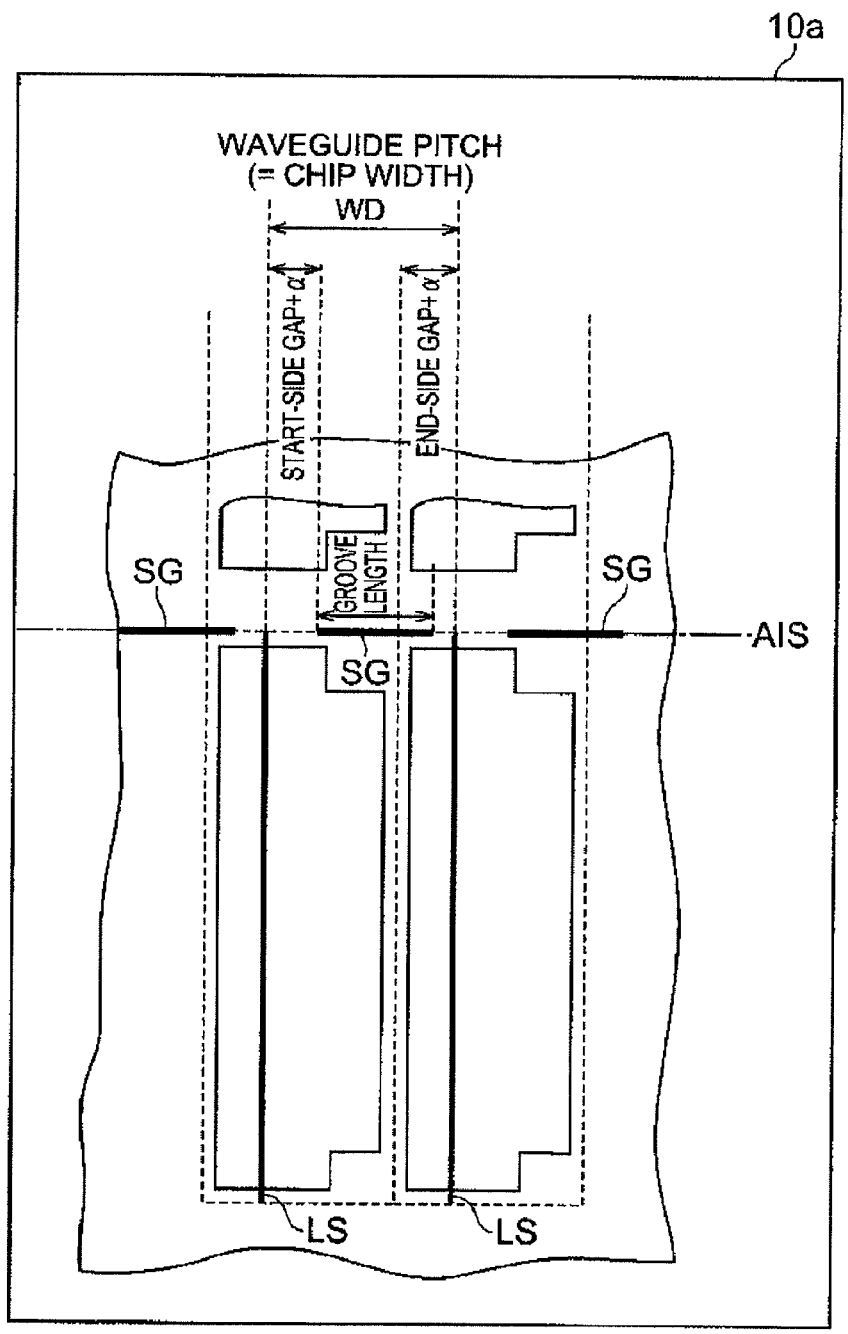
FIG. 18 is a drawing showing an arrangement of scribed grooves SG and laser stripes LS.

FIG. 17 is a list of dimensions of scribed grooves in an experiment conducted for obtaining the chip widths of 200 µm, 150 µm, and 100 µm. FIG. 18 is a drawing showing an arrangement of scribed grooves SG and laser stripes LS. The end-side space corresponds to the distance W1 and the start-side space to the distance W2. On the start side, a space of 30 µm to the waveguide is necessary in order to avoid damage. On the end side, a space of 10 µm is necessary because of a problem of positional accuracy. Therefore, the minimum groove pitch is 40 µm. Unless the bottom surface of the scribed groove is the ship bottom shape, repeatability of groove depth becomes worse, and thus the minimum groove length is 40 µm. The "margin of +α" means a room for minimizing the adverse effect of debris. In fabrication of devices with the chip width, for example, of 100 µm-200 µm, the dimensional ranges of the shape of the scribed groove are estimated as described below.

| chip width, | length of scribed groove, | scribed groove pitch, |
|---|---|---|
| 200 µm, | 40 µm-160 µm, | 160-40 µm, |
| 150 µm, | 40 µm-110 µm, | 110-40 µm, |
| 200 µm, | 40 µm-60 µm, | 60-40 µm |

In this estimation the minimum length of the scribed groove is 40 µm. When the length of the scribed groove is not less than 40 µm, the fractured face has sufficient perpendicularity.

EXAMPLE 5

A laser diode is grown by metal-organic vapor phase epitaxy as follows. The raw materials used herein are trimethyl gallium (TMGa), trimethyl aluminum (TMAl), trimethyl indium (TMIn), ammonia ($NH_3$), and silane ($SiH_4$). The substrate used is a {20-21}-plane GaN substrate grown by HVPE.

This substrate is placed on a susceptor in a reaction furnace, and epitaxial layers are grown according to the following growth procedure. First, an n-type GaN layer is grown in the thickness of 1000 nm. Next, an n-type InAlGaN cladding layer is grown in the thickness of 1200 nm on the n-type GaN layer. Subsequently, an n-type GaN guide layer and an n-type InGaN guide layer are grown in the thickness of 250 nm and in the thickness of 115 nm, respectively, and thereafter a two-cycle MQW is grown in the configuration of GaN barrier layers (10 nm thick)/InGaN well layers (3 nm thick). Then grown are an undoped InGaN guide layer in the thickness of 65 nm, a p-type AlGaN block layer in the thickness of 20 nm, a p-type InGaN guide layer in the thickness of 50 nm, and a p-type GaN guide layer in the thickness of 250 nm. Next, a p-type InAlGaN cladding layer is grown in the thickness of 400 nm. Finally, a p-type GaN contact layer is grown in the thickness of 50 nm. An epitaxial substrate is produced through the procedure of these steps.

An insulating film of $SiO_2$ is deposited on the contact layer, and thereafter, the photolithography is used to form a stripe window in the width of 10 µm by wet etching. The laser stripe is provided in parallel with the projected direction of the c-axis on the principal surface. The angle between the waveguide vector and the c-axis vector is not more than 0.1°. After formation of the stripe window, a p-side electrode of Ni/Au and a pad electrode of Ti/Au are deposited by vapor deposition. Thereafter, the back surface of the GaN substrate (GaN wafer) is polished using diamond slurry to produce a substrate product with the back surface in a mirror state. An n-side electrode of Ti/Al/Ti/Au is formed by vapor deposition on the back surface (polished surface) of the GaN substrate (GaN wafer). The substrate product for the gain guiding type laser shown in FIG. 19 can be fabricated according to the procedure of these steps.

Figure 20:
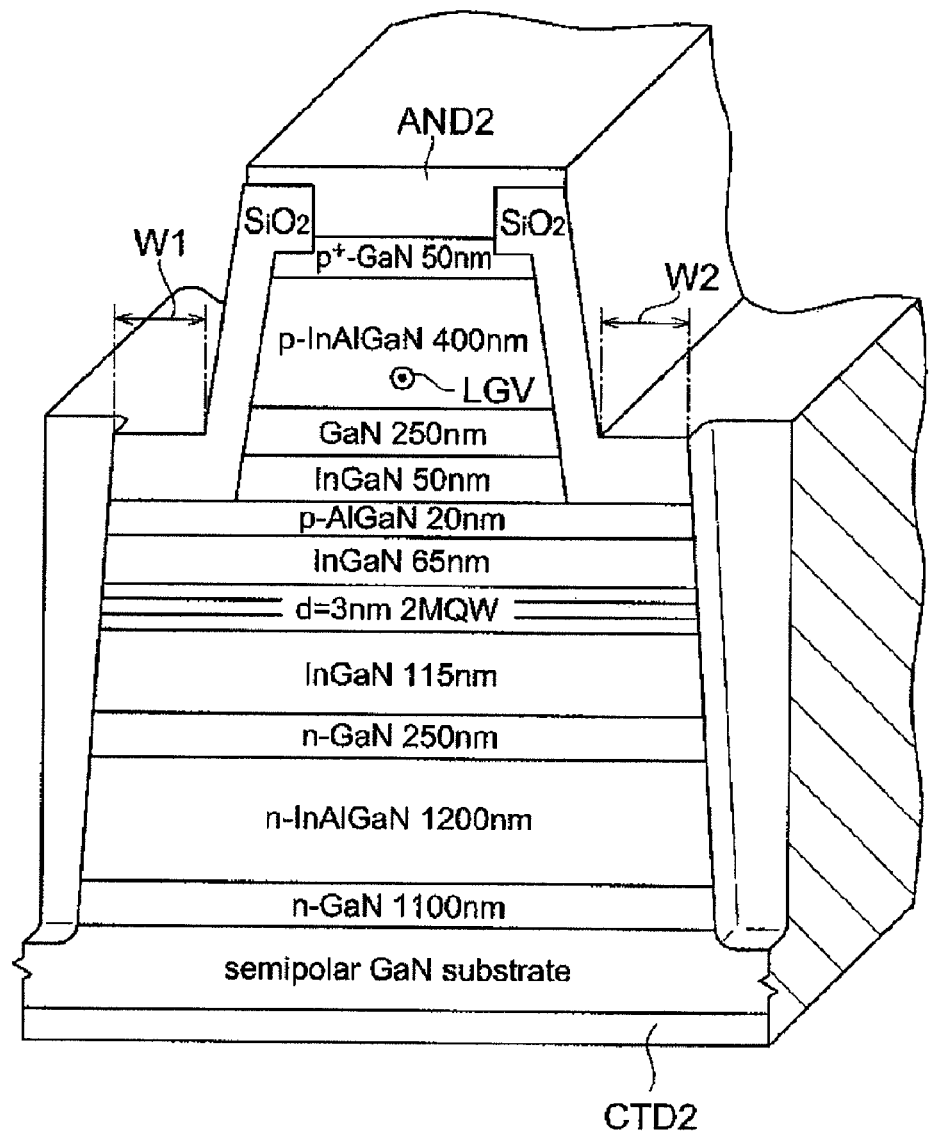
FIG. 20 is a drawing schematically showing an example of an index guided laser having the ridge structure.

It is also possible to fabricate an index guided laser with the ridge structure shown in FIG. 20, by the following method. For producing the ridge structure in the width of 2 µm, a mask of a positive resist with a pattern in the width of 2 µm is provided by photolithography. The laser waveguide is directed so as to be parallel to the direction of the projected component as a projection of the c-axis vector on the principal surface. The ridge structure is produced by dry etching using $Cl_2$. The etching depth is, for example, 0.7 µm, and the etching of the semiconductor region of the epitaxial substrate is carried on until the AlGaN block layer becomes exposed. After the etching, the resist mask is removed. The stripe mask in the width of about 2 µm is left on the ridge structure by photolithography. The direction of the stripe mask is aligned with the direction of the ridge structure.

Figure 19:
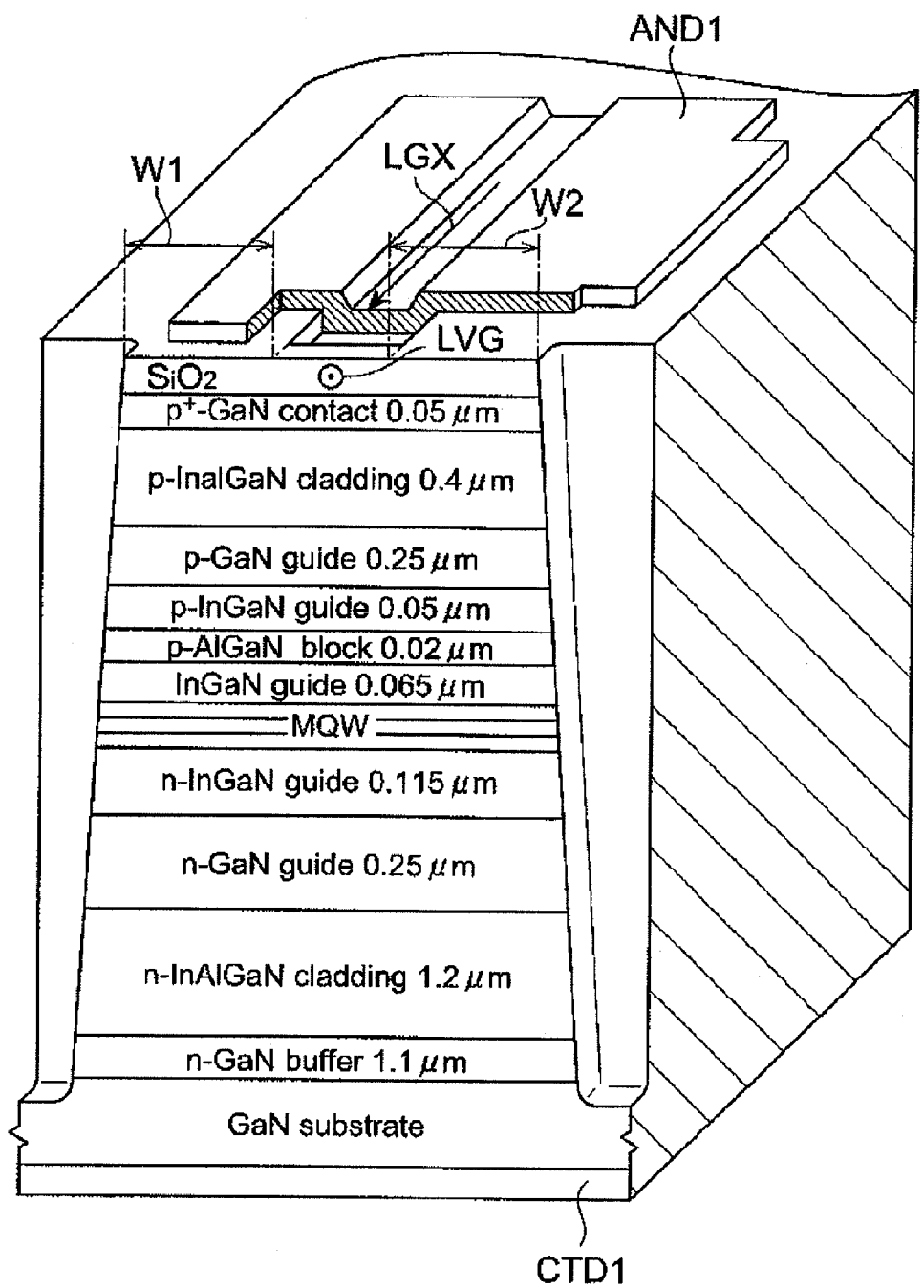
FIG. 19 is a drawing schematically showing an example of a semiconductor laser having the gain guiding structure.

After this, $SiO_2$ is deposited by vacuum vapor deposition on the side faces of the ridge. After the vapor deposition of the insulating film, $SiO_2$ on the ridge is removed by the lift-off method to form the insulating film with the striped aperture. Next, an anode electrode AND2 and a cathode electrode CTD2 are formed to obtain the substrate product. The scribed grooves to be formed in a subsequent step are also depicted in FIGS. 19 and 20.

The cavity mirrors for these laser stripes are produced with a laser scriber using the YAG laser at the wavelength of 355 nm. The lasing chip yield can be higher in the case where the scribed grooves are formed with the laser scriber, followed by break, than in the case using the diamond scribing method. The conditions for formation of the scribed grooves are as follows.

Laser beam output: 100 mW.
Scan speed: 5 mm/s.

The scribed grooves thus formed are grooves, for example, having the length of 100 µm, the width of 10 µm, and the depth of 40 µm. In the formation of scribed grooves, the laser scriber is controlled so that the groove pitch becomes 50-300 µm, and the laser scriber is controlled so that the distances between the scribed groove ends and the waveguide become in a range of 10 to 300 µm. The scribed grooves are periodically formed by direct irradiation with the laser beam through the aperture of the electrode to the surface of the substrate. The cavity length is 600 µm. The definitions of the distances W1, W2 are shown in FIGS. 19 and 20 as described above.

A blade is used to press against the back surface of the substrate to produce the cavity mirrors by fracture. A laser bar is produced by breaking the substrate by press at the end on the back side of the substrate. The method of using as the mirror surfaces the end faces perpendicular to the waveguide provided in parallel with the projected direction of the c-axis on the semipolar principal surface is different from the conventional cleaved facets such as m-planes, a-planes, or c-planes which are used as the end faces in lasers such as the conventional c-planes or m-planes. A scribed groove (with the groove length of 100 μm and the groove pitch of 300 μm) in the laser bar is observed from a cross section thereof. There is no contrast observed in either of a secondary electron image (SE image) and a CL image, at the terminal end of the scribed groove. On the other hand, there is a contrast observed in the secondary electron image of the start portion of the scribed groove, and it is shown that the semiconductor region near the scribed groove is altered in a level to change the secondary electron emission rate. There is also a contrast seen in the CL image, and the altered region in the SE image is observed as a non-radiative region.

The end faces of the laser bar thus produced are coated with a dielectric multilayer film by vacuum vapor deposition. The dielectric multilayer film is composed of an alternate stack of $SiO_2$ and $TiO_2$. The thickness of each layer is adjusted in a range of 50-100 nm and designed so that the center wavelength of reflectance falls within a range of 500-530 nm. The reflecting surface on one side consisted of ten cycles and the designed value of reflectance is about 95%. The reflecting surface on the other side consisted of six cycles and the designed value of reflectance is about 80%.

Evaluation by energization is conducted at room temperature. A power supply used is a pulsed power supply with the pulse width of 500 ns and the duty ratio of 0.1%, and the energization is conducted with needles on the surface electrodes. In measurement of optical output, the emission from the end face of the laser bar is detected with a photodiode to check the current-optical output characteristic (I-L characteristic). In measurement of emission wavelength, the emission from the end face of the laser bar is made to pass through an optical fiber, and a spectrum thereof is measured with a spectrum analyzer as a detector. The lasing wavelength is 500-530 nm.

Figure 21:
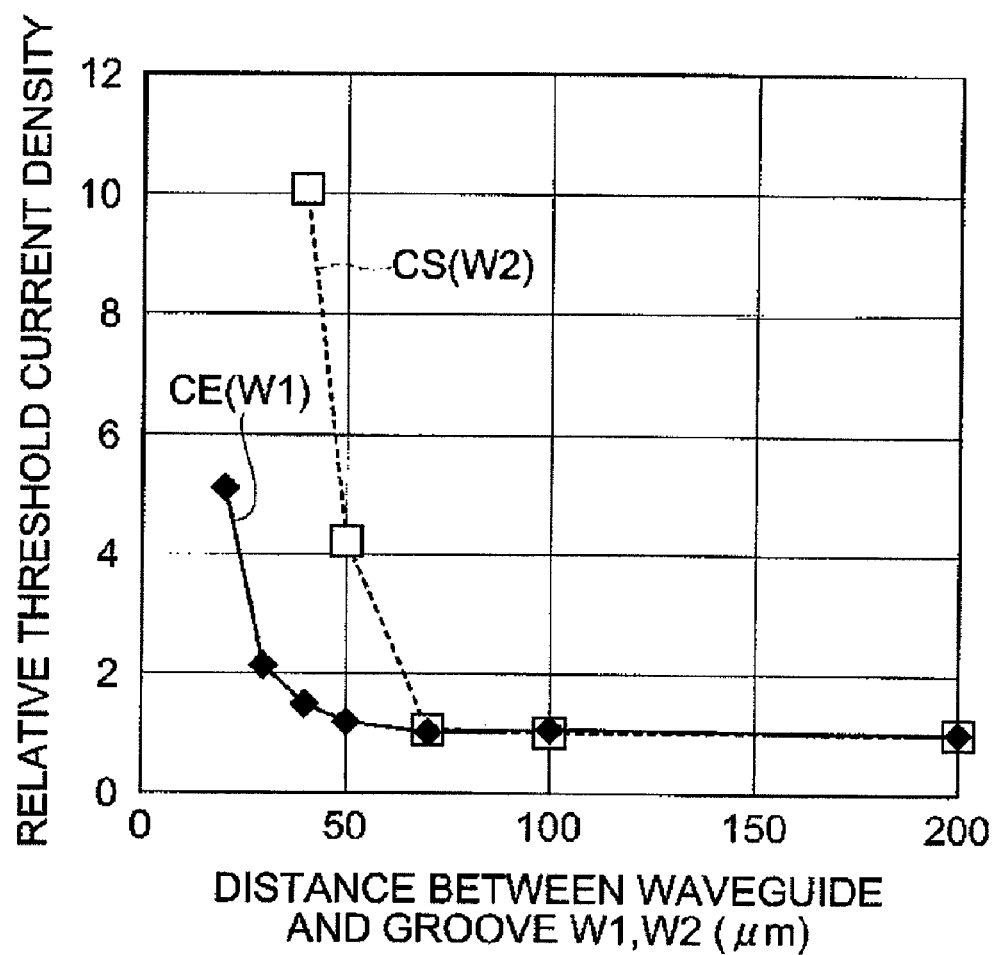
FIG. 21 is a drawing showing dependence of lasing yield on distances between a waveguide and scribed grooves.

An investigation is carried out to investigate dependence of lasing yield on the distances between the waveguide and grooves. FIG. 21 shows the dependence of lasing yield on the distances between the waveguide and the scribed grooves. The relative threshold current density on the vertical axis is defined by an increase rate from an intermediate value of oscillation threshold current density in a hundred chips of laser devices. A characteristic curve CS represents a relation of the distance between the start end of the scribed groove and the waveguide versus lasing yield, and a characteristic curve CE represents a relation of the distance between the terminal end of the scribed groove and the waveguide versus lasing yield. With reference to FIG. 21, when the terminal end is made closer to the waveguide and when the distance W1 is not less than 20 μm, the lasing yield is improved, without degradation of the laser characteristic. On the other hand, when the start end is made closer to the waveguide and when the distance W2 is not less than 50 μm, the lasing yield becomes deteriorated with degradation of the characteristic. From this result, the terminal end with little damage can be located closer up to the distance of not more than 70 μm from the waveguide, and the distance can be not less than 20 μm. This allows reduction in chip width. For this reason, the number of chips taken increases, so as to reduce cost.

EXAMPLE 6

In Example 2, the plurality of epitaxial films for the semiconductor laser is grown on the GaN substrate having the {20-21} plane. The end faces for the optical cavity are formed by the formation of scribed grooves and the press as described above. In order to find candidates for these end faces, plane orientations making an angle near 90° to the (20-21) plane and being different from the a-plane are determined by calculation. With reference to FIG. 22, the following angles and plane orientations have angles near 90° to the (20-21) plane.

| specific plane index, | angle to {20-21} plane, |
|---|---|
| (-1016), | 92.46°, |
| (-1017), | 90.10°, |
| (-1018), | 88.29° |

Figure 23:
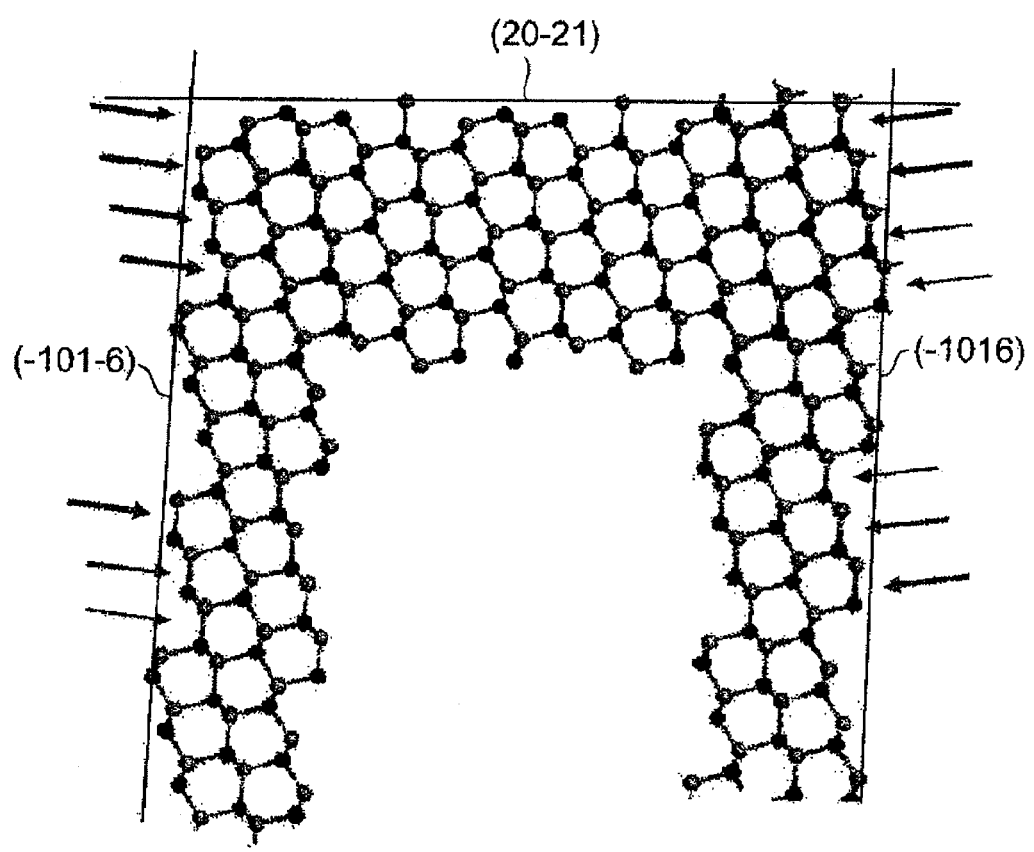
FIG. 23 is a drawing showing atomic arrangements in (20-21) plane, (−101-6) plane, and (−1016) plane.
Figure 24:
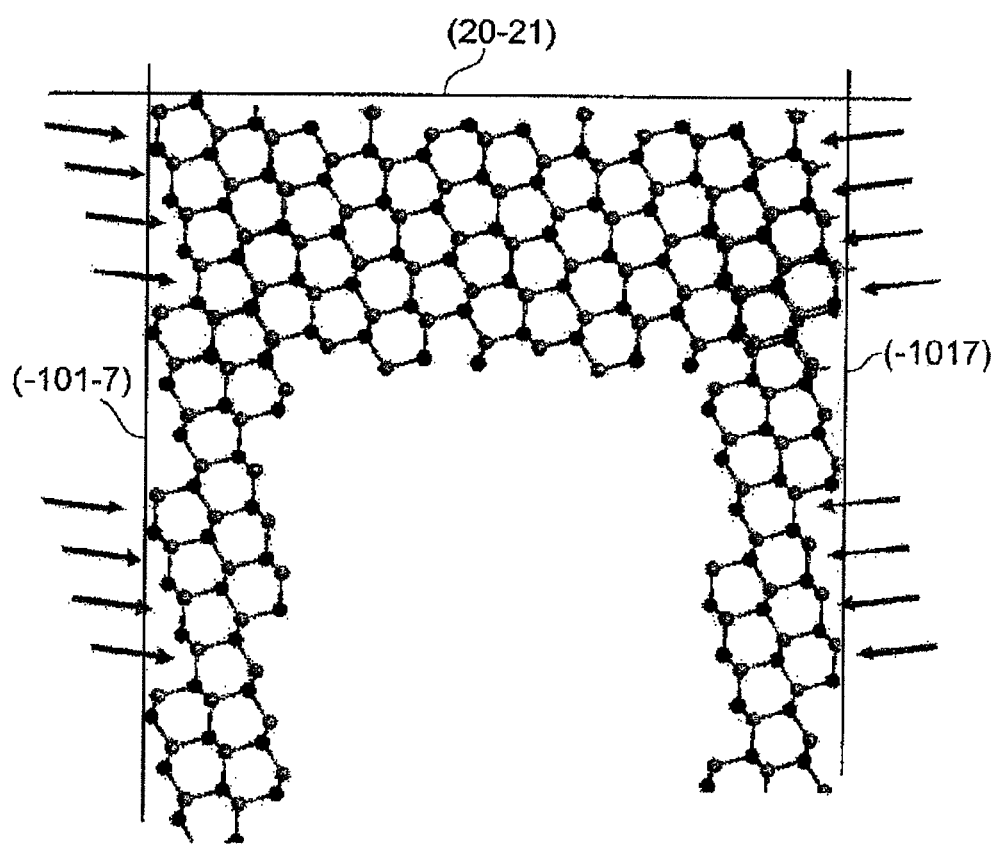
FIG. 24 is a drawing showing atomic arrangements in (20-21) plane, (−101-7) plane, and (−1017) plane.
Figure 25:
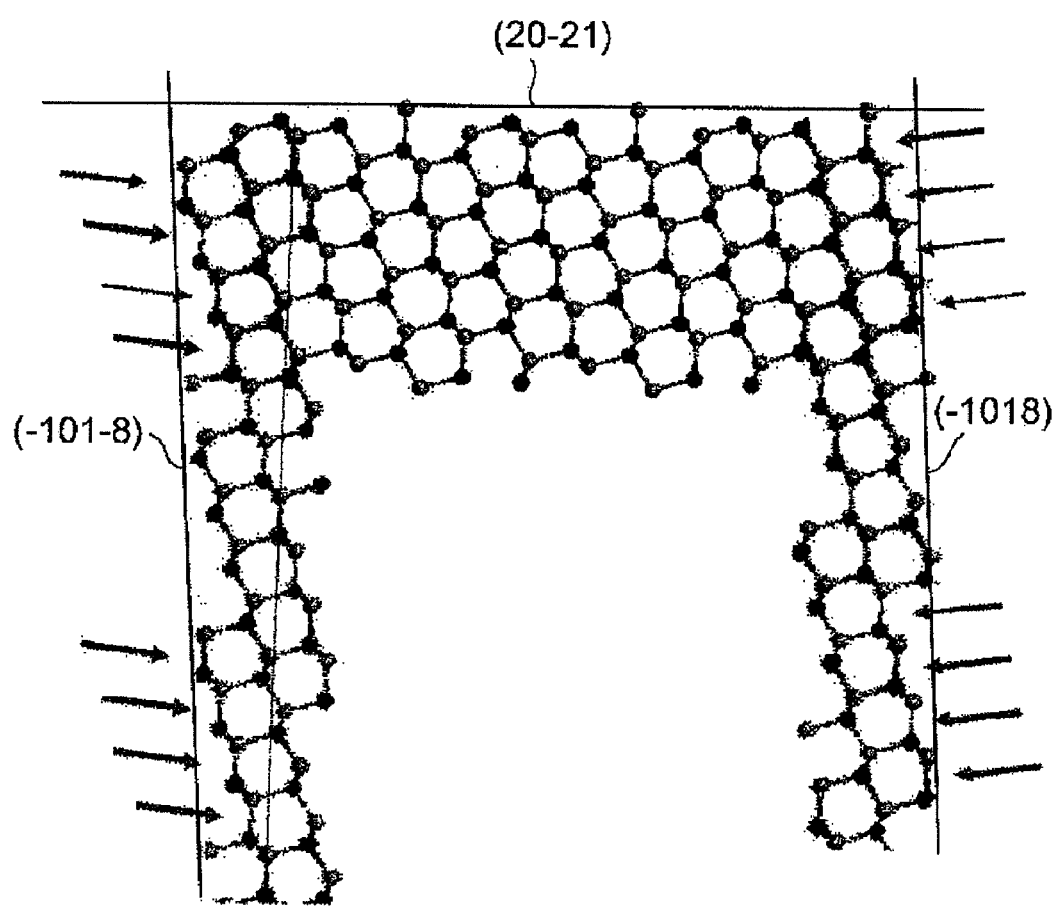
FIG. 25 is a drawing showing atomic arrangements in (20-21) plane, (−101-8) plane, and (−1018) plane.

FIG. 23 is a drawing showing atomic arrangements in the (20-21) plane, (-101-6) plane, and (-1016) plane. FIG. 24 is a drawing showing atomic arrangements in the (20-21) plane, (-101-7) plane, and (-1017) plane. FIG. 25 is a drawing showing atomic arrangements in the (20-21) plane, (-101-8) plane, and (-1018) plane. As shown in FIGS. 23 to 25, local atom arrangements indicated by arrows show configurations of neutral atoms in terms of charge, and electrically neutral atom arrangements appear periodically. The reason why the relatively normal faces are obtained to the grown surface can be that generation of fractured faces is considered to be relatively stable because of the periodic appearance of the neutral atomic configurations in terms of charge.

According to various experiments including the above-described Examples 1 to 6, the angle ALPHA can be in a range of not less than 45° and not more than 80° or in a range of not less than 100° and not more than 135°. In order to improve the lasing chip yield, the angle ALPHA can be in a range of not less than 63° and not more than 80° or in a range of not less than 100° and not more than 117°. The typical semipolar principal surface can be any one of the {20-21} plane, {10-11} plane, {20-2-1} plane, and {10-1-1} plane. Furthermore, the principal surface can be a slight slant surface from these semipolar planes. For example, the semipolar principal surface can be a slight slant surface off in a range of not less than −4° and not more than +4° toward the m-plane from any one of the {20-21} plane, {10-11} plane, {20-2-1} plane, and {10-1-1} plane.

As described above, the embodiment provides a III-nitride semiconductor laser device with a laser cavity enabling a low threshold current, on a semipolar plane of a support base tilting from the c-axis toward the m-axis of a hexagonal III-nitride. The embodiment provides a method for fabricating the III-nitride semiconductor laser device. The embodiment provides a method for estimating damage from formation of a scribe groove in a semiconductor laser device.

Described and illustrated the principle of the invention in a preferred embodiment thereof, it is appreciated by those having skill in the art that the invention can be modified in arrangement and detail without departing from such principles. Although a light emitting device is described for illustrative purposes in the embodiments, a p-side electrode of electronic devices such as transistors and diodes is also available. We therefore claim all modifications and variations coming within the spirit and scope of the following claims.

What is claimed is:

1. A group-III nitride semiconductor laser device comprising:
a laser structure including a support base and a semiconductor region, the support base comprising a hexagonal group-III nitride semiconductor and having a semipolar principal surface, the semiconductor region being provided on the semipolar principal surface of the support base; and an electrode being provided on the semiconductor region of the laser structure, wherein an angle between the normal axis and a c-axis of the hexagonal group-III nitride semiconductor is in a range of not less than 45° and not more than 80° or in a range of not less than 100° and not more than 135°, wherein the semiconductor region includes a first cladding layer comprising a first conductivity type gallium nitride (GaN)-based semiconductor, a second cladding layer comprising a second conductivity type GaN-based semiconductor, and an active layer being provided between the first cladding layer and the second cladding layer, wherein the first cladding layer, the second cladding layer, and the active layer are arranged along the normal axis to the semipolar principal surface, wherein the active layer includes a GaN-based semiconductor layer, wherein the c-axis of the hexagonal group-III nitride semiconductor of the support base tilts at an angle ALPHA with respect to the normal axis toward an m-axis of the hexagonal group-III nitride semiconductor, wherein the laser structure includes first and second fractured faces intersecting with an m-n plane defined by the m-axis of the hexagonal group-III nitride semiconductor and the normal axis, wherein a laser cavity of the group-III nitride semiconductor laser device includes the first and second fractured faces, wherein each of the first and second fractured faces extends from an edge of the first surface to an edge of the second surface, wherein the laser structure includes first and second surfaces, and the first surface is a surface opposite to the second surface, wherein the semiconductor region is located between the first surface and the substrate, wherein the laser structure includes a laser stripe extending in a direction of a waveguide axis above the semipolar principal surface of the support base, and the waveguide axis extends from one to the other of the first and second fractured faces, wherein the laser structure has first and second recesses provided each at a portion of the edge of the first surface in the first fractured face, the first and second recesses extend from the first surface of the laser structure, and bottom ends of the first and second recesses are located apart from the edge of the second surface of the laser structure, wherein the first recess has an end at the first surface, and the second recess has an end at the first surface, and wherein a first distance between the laser stripe and the end of the first recess is smaller than a second distance between the laser stripe and the end of the second recess.

2. The group-III nitride semiconductor laser device according to claim 1, wherein the first and second recesses are provided along a predetermined a-n plane defined by an a-axis of the hexagonal group-III nitride semiconductor and the normal axis.

3. The group-III nitride semiconductor laser device according to claim 1, wherein the first distance is not less than 20 μm and less than 50 μm.

4. The group-III nitride semiconductor laser device according to claim 1, wherein the first distance is less than 50 μm, and the second distance is not less than 50 μm.

5. The group-III nitride semiconductor laser device according to claim 1, wherein a width of the group-III nitride semiconductor laser device is not more than 200 μm.

6. The group-III nitride semiconductor laser device according to claim 1, wherein an end face of the support base and an end face of the semiconductor region are exposed in each of the first and second fractured faces, and wherein an angle between the end face of the semiconductor region in the active layer and a reference plane perpendicular to the m-axis of the support base comprising the hexagonal nitride semiconductor is an angle in a range of not less than (ALPHA−5)° and not more than (ALPHA+5)° on a first plane defined by the c-axis and the m-axis of the group-III nitride semiconductor.

7. The group-III nitride semiconductor laser device according to claim 1, wherein the angle is in a range of not less than −5° and not more than +5° on a second plane perpendicular to the first plane and the normal axis.

8. The group-III nitride semiconductor laser device according to claim 1, wherein an angle between the normal axis and the c-axis of the hexagonal group-III nitride semiconductor falls within a range of not less than 63° and not more than 80° or within a range of not less than 100° and not more than 117°.

9. The group-III nitride semiconductor laser device according to claim 1, wherein a thickness of the support base is not more than 400 μm.

10. The group-III nitride semiconductor laser device according to claim 1, wherein a thickness of the support base is not less than 50 μm and not more than 100 μm.

11. The group-III nitride semiconductor laser device according to claim 1, wherein laser light from the active layer is polarized in a direction of an a-axis of the hexagonal group-III nitride semiconductor.

12. The group-III nitride semiconductor laser device according to claim 1, wherein light in the LED mode in the group-III nitride semiconductor laser device includes a polarization component I1 in the direction of an a-axis of the hexagonal group-III nitride semiconductor, and a polarization component I2 in a projected direction of the c-axis of the hexagonal group-III nitride semiconductor on the principal surface, the polarization component I1 being greater than the polarization component I2.

13. The group-III nitride semiconductor laser device according to claim 1, wherein the semipolar principal surface is a surface with a slight slant in a range of not less than −4° and not more than +4° off from any one semipolar plane of a {20-21} plane, a {10-11} plane, a {20-2-1} plane, and a {10-1-1} plane.

14. The group-III nitride semiconductor laser device according to claim 1, wherein the semipolar principal surface is one of a {20-21} plane, a {10-11} plane, a {20-2-1} plane, and a {10-1-1} plane.

15. The group-III nitride semiconductor laser device according to claim 1, wherein a stacking fault density of the support base is not more than $1 \times 10^4$ cm$^{-1}$.

16. The group-III nitride semiconductor laser device according to claim 1, wherein the support base comprises any one of GaN, AlGaN, AlN, InGaN, and InAlGaN.

17. The group-III nitride semiconductor laser device according to claim 1, further comprising a dielectric multilayer film provided on at least one of the first and second fractured faces.

18. The group-III nitride semiconductor laser device according to claim 1, wherein the active layer includes a light emitting region provided so as to generate light at a wavelength of not less than 430 nm and not more than 600 nm.

19. The group-III nitride semiconductor laser device according to claim 1, wherein the active layer includes a quantum well structure provided so as to generate light at a wavelength of not less than 500 nm and not more than 600 nm.

20. The group-III nitride semiconductor laser device according to claim 1, wherein the laser structure further comprises an insulating film with an aperture, insulating film being provided on the semiconductor region,
   wherein the electrode is connected through the aperture of the insulating film to the semiconductor region of the laser structure,
   wherein the first distance is defined by a distance between the aperture of the insulating film and the end of the first recess, and
   wherein the second distance is defined by a distance between the aperture of the insulating film and the end of the second recess.

21. The group-III nitride semiconductor laser device according to claim 1, wherein the semiconductor region of the laser structure has a ridge structure,
   wherein the first distance is defined by a distance between the ridge structure and the end of the first recess, and
   wherein the second distance is defined by a distance between the ridge structure and the end of the second recess.

22. The group-III nitride semiconductor laser device according to claim 1, wherein the first recess includes a first slope portion where the bottom end of the first recess tilts toward the end of the first recess,
   wherein the second recess includes a second slope portion where the bottom end of the second recess tilts toward the end of the second recess, and
   wherein a length of the first slope portion is longer than a length of the second slope portion.

23. A group-III nitride semiconductor laser device comprising:
   a laser structure including a support base and a semiconductor region, the support base comprising a hexagonal group-III nitride semiconductor and having a semipolar principal surface and a back surface, the semiconductor region being provided on the semipolar principal surface of the support base; and
   an electrode being provided on the semiconductor region of the laser structure,
   wherein the semiconductor region includes a first conductivity type cladding layer, a second conductivity type cladding layer, and an active layer, the active layer being provided between the first cladding layer and the second cladding layer,
   wherein the first conductivity type cladding layer, the second conductivity type cladding layer, and the active layer are arranged along a normal axis to the semipolar principal surface,
   wherein a c-axis of the hexagonal group-III nitride semiconductor of the support base tilts at an angle ALPHA with respect to the normal axis toward an m-axis of the hexagonal group-III nitride semiconductor,
   wherein the angle ALPHA is in a range of not less than 45° and not more than 80° or in a range of not less than 100° and not more than 135°,
   wherein the laser structure includes first and second surfaces,
   wherein the first surface is a surface opposite to the second surface,
   wherein the semiconductor region is located between the first surface and the support base,
   wherein the laser structure has first and second scribed marks provided at one end and the other end, respectively, of an edge of the first surface at an end of the laser structure,
   wherein the first and second scribed marks extend along an a-n plane defined by an a-axis of the hexagonal group-III nitride semiconductor and the normal axis,
   wherein the first and second scribed marks extend from the first surface,
   wherein the end of the laser structure has a fractured face connecting edges of the first and second scribed marks and edges of the first and second surfaces of the laser structure,
   wherein a laser cavity of the group-III nitride semiconductor laser device includes the fractured face,
   wherein the laser structure includes a laser stripe extending in a direction of a waveguide axis above the semipolar principal surface of the support base,
   wherein the first scribed mark has an end at the first surface,
   wherein the second scribed mark has an end at the first surface, and
   wherein a first distance between the laser stripe and the end of the first scribed mark is smaller than a second distance between the laser stripe and the end of the second scribed mark.

* * * * *